US012297507B2

(12) United States Patent
Lu et al.

(10) Patent No.: US 12,297,507 B2
(45) Date of Patent: May 13, 2025

(54) BIOMARKERS FOR HEAD AND NECK CANCER AND METHODS OF THEIR USE

(71) Applicant: The Regents of the University of Colorado, a body corporate, Denver, CO (US)

(72) Inventors: Shi-Long Lu, Greenwood Village, CO (US); John Song, Denver, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

(21) Appl. No.: 17/817,452

(22) Filed: Aug. 4, 2022

(65) Prior Publication Data
US 2023/0071575 A1 Mar. 9, 2023

Related U.S. Application Data

(62) Division of application No. 16/857,767, filed on Apr. 24, 2020, now Pat. No. 11,441,193, which is a division of application No. 15/519,758, filed as application No. PCT/US2015/055958 on Oct. 16, 2015, now Pat. No. 10,640,831.

(60) Provisional application No. 62/065,122, filed on Oct. 17, 2014.

(51) Int. Cl.
*C12Q 1/6886* (2018.01)
*C12Q 1/70* (2006.01)

(52) U.S. Cl.
CPC ............ *C12Q 1/6886* (2013.01); *C12Q 1/708* (2013.01); *C12Q 2600/154* (2013.01); *C12Q 2600/156* (2013.01); *C12Q 2600/178* (2013.01)

(58) Field of Classification Search
None
See application file for complete search history.

(56) References Cited

U.S. PATENT DOCUMENTS

| 9,890,432 | B2 | 2/2018 | Meijer et al. |
| 2013/0303826 | A1 | 11/2013 | Jurisica et al. |
| 2014/0271455 | A1 | 9/2014 | Pfeifer et al. |

FOREIGN PATENT DOCUMENTS

| CN | 103857796 | 6/2014 |
| EP | 2757154 | 7/2014 |
| WO | WO 200070090 | 11/2000 |
| WO | WO 2013039394 | 3/2013 |

OTHER PUBLICATIONS

Langevin et al. (Cancer Apr. 1, 2011 p. 1454) (Year: 2011).*
Diffenbach (PCR methods and Applications (1993) vol. 3, pp. S30-S37) (Year: 1993).*
Roux et al(PCR Methods and Applications (1995) vol. 4, pp. s185-s194) (Year: 1995).*
Chinese Patent Application No. 202110552040.7 First Office Action dated Aug. 21, 2023 with English translation, 23 pages.
Green et al. (Otolaryngology-Head and Neck Surgery 2013;149(2 suppl):P61-P61) (Year: 2013).
Chinese Patent Application No. 201580056428.0, Office Action dated Nov. 24, 2020, 3 pages.
Chinese Patent Application No. 201580056428.0, English translation of Office Action dated Aug. 12, 2020, 6 pages.
Ambros V. The functions of animal microRNAs. Nature. 2004;431(7006):350-5.
Babu, J. M.; Prathibha, R.; Jijith, V. S.; Hariharan, R.; Pillai, M. R., A miR-centric view of head and neck cancers. Biochim Biophys Acta 2011, 1816 (1), 67-72.
Betel, D., Wilson, M., Gabow, A., Marks, D. S. & Sander, C. The microRNA.org resource: targets and expression. Nucleic Acids Res. 36, D149-D153 (2008).
Boyle JO, Mao L, Brennan JA, et al. Gene mutations in saliva as molecular markers for head and neck squamous cell carcinomas. Am J Surg. 1994;168(5):429-32.
Chinese Patent Application No. 201580056428.0, Office Action dated Feb. 7, 2020, 12 pages.
Croce, C. M., Causes and consequences of microRNA dysregulation in cancer. Nat Rev Genet 2009, 10 (10), 704-14.
Friedman, R. C., Farh, K. K., Burge, C. B. & Bartel, D. P. Most mammalian mRNAs are conserved targets of microRNAs. Genome Res. 19, 92-105 (2009).
Gangaraju, V. K.; Lin, H., MicroRNAs: key regulators of stem cells. Nat Rev Mol Cell Biol 2009, 10 (2), 116-25.
Garzon R, Marcucci G, Croce CM. Targeting microRNAs in cancer: rationale, strategies and challenges. Nat Rev Drug Discov. 2010;9(10):775-89.
Ha, P. K.; Califano, J. A., Promoter methylation and inactivation of tumour-suppressor genes in oral squamous-cell carcinoma. Lancet Oncol 2006, 7 (1), 77-82.
Hildebrandt, M. A.; Gu, J.; Lin, J.; Ye, Y.; Tan, W.; Tamboli, P.; Wood, C. G.; Wu, X., Hsa-miR-9 methylation status is associated with cancer development and metastatic recurrence in patients with clear cell renal cell carcinoma. Oncogene 29 (42), 5724-8.
Iorio, M. V.; Croce, C. M., MicroRNA dysregulation in cancer: diagnostics, monitoring and therapeutics. A comprehensive review. EMBO Mol Med 2012, 4 (3), 143-59.
Iorio, M. V.; Piovan, C.; Croce, C. M., Interplay between microRNAs and the epigenetic machinery: an intricate network. Biochim Biophys Acta 2010, 1799 (10-12), 694-701.
Jemal, A.; Siegel, R.; Ward, E.; Hao, Y.; Xu, J.; Thun, M. J., Cancer statistics, 2009. CA: a cancer journal for clinicians 2009, 59 (4), 225-49.

(Continued)

Primary Examiner — Katherine D Salmon
(74) Attorney, Agent, or Firm — COZEN O'CONNOR

(57) ABSTRACT

Disclosed is a diagnostic panel of methylated genomic loci encoding microRNA (mgmiR) markers that demonstrated 90% sensitivity and 100% specificity in the detection of head and neck squamous cell carcinoma (HNSCC). These results represent the first use of quantitative MS-PCR for the detection of mgmiRs. In addition, this panel demonstrates the ability to detect hypermethylation in the adjacent mucosa of cancer patients, suggesting its utility in early detection. This panel is also capable of detecting cancer by using saliva, blood and FNA tissue samples.

4 Claims, 17 Drawing Sheets

Specification includes a Sequence Listing.

(56) References Cited

OTHER PUBLICATIONS

Jones, P. A.; Baylin, S. B., The epigenomics of cancer. Cell 2007, 128 (4), 683-92.
Krek, D. et al. Combinatorial microRNA target predictions. Nature Genet. 37, 495-500 (2005).
Langevin (2010) "MicroRNA-137 promoter methylation in oral rinses from patients with squamous cell carcinoma of the head and neck is associated with gender and body mass index", Carcinogenesis, 31:5, pp. 864-870.
Lee RC, Feinbaum RL, Ambros V. The C. elegans heterochronic gene lin-4 encodes small RNAs with antisense complementarity to lin-14. Cell. 1993;75(5):843-54.
Lewis, B. Shih, I. Jones-Rhoades, M., Bartel, D.& Burge, C. Prediction of mammalian microRNA targets. Cell 115, 787-798 (2003).
Lujambio, A.; Calin, G. A.; Villanueva, A.; Ropero, S.; Sanchez-Cespedes, M.; Blanco, D.; Montuenga, L. M.; Rossi, S.; Nicoloso, M. S.; Faller, W. J.; Gallagher, W. M.; Eccles, S. A.; Croce, C. M.; Esteller, M., A microRNA DNA methylation signature for human cancer metastasis. *Proc Natl Acad Sci U S A* 2008, 105 (36), 13556-61.
Minor J, Wang X, Zhang F, et al. Methylation of microRNA-9 is a specific and sensitive biomarker for oral and oropharyngeal squamous cell carcinomas. Oral Oncol. 2012;48(1):73-8.
Minor, J.; Wang, X.; Zhang, F.; Song, J.; Jimeno, A.; Wang, X. J.; Lu, X.; Gross, N.; Kulesz- Martin, M.; Wang, D.; Lu, S. L., Methylation of microRNA-9 is a specific and sensitive biomarker for oral and oropharyngeal squamous cell carcinomas. *Oral Oncol* 2012, 48 (1), 73-8.
PCT/US2015/055958 International Search Report & Written Opinion mailed Jan. 20, 2016.
Roh, J. L.; Westra, W. H.; Califano, J. A.; Sidransky, D.; Koch, W. M., Tissue imprint for molecular mapping of deep surgical margins in patients with head and neck squamous cell carcinoma. *Head Neck* 2012, 34 (11), 1529-36.
Rosenfeld, N.; Aharonov, R.; Meiri, E.; Rosenwald, S.; Spector, Y.; Zepeniuk, M.; Benjamin, H.; Shabes, N.; Tabak, S.; Levy, A.; Lebanony, D.; Goren, Y.; Silberschein, E.; Targan, N.; Ben-An, A.; Gilad, S.; Sion-Vardy, N.; Tobar, A.; Feinmesser, M.; Kharenko, O.; Nativ, O.; Nass, D.; Perelman, M.; Yosepovich, A.; Shalmon, B.; Polak-Charcon, S.; Fridman, E.; Avniel, A.; Bentwich, I.; Bentwich, Z.; Cohen, D.; Chajut, A.; Barshack, I., MicroRNAs accurately identify cancer tissue origin. *Nat Biotechnol* 2008, 26 (4), 462-9.
Saito, Y.; Jones, P. A., Epigenetic activation of tumor suppressor microRNAs in human cancer cells. *Cell Cycle* 2006, 5 (19), 2220-2.
Saito, Y.; Liang, G.; Egger, G.; Friedman, J. M.; Chuang, J. C.; Coetzee, G. A.; Jones, P. A., Specific activation of microRNA-127 with downregulation of the proto-oncogene BCL6 by chromatin-modifying drugs in human cancer cells. *Cancer Cell* 2006, 9 (6), 435-43.
Siegel, R.; Naishadham, D.; Jemal, A., Cancer statistics, 2013. CA: *a cancer journal for clinicians* 2013, 63 (1), 11-30.
Watson JD, Crick FH. Molecular structure of nucleic acids; a structure for deoxyribose nucleic acid. Nature. 1953;171(4356):737-8.
Worsham MJ, Ali H, Dragovic J, Schweitzer VP. Molecular characterization of head and neck cancer: how close to personalized targeted therapy?. Mol Diagn Ther. 2012;16(4):209-22.
Worsham MJ, Chen KM, Ghanem T, Stephen JK, Divine G. Epigenetic modulation of signal transduction pathways in HPV-associated HNSCC. Otolaryngol Head Neck Surg. 2013;149(3):409-16.
Chinese Patent Application No. 202110552040.7, Office Action dated Apr. 28, 2024, with English translation, 10 pages.

* cited by examiner

| Tumor | mgmiR 124-1 | mgmiR 124-2 | mgmiR 124-3 | mgmiR 137 | mgmiR 9-1 | mgmiR 9-3 |
|---|---|---|---|---|---|---|
| 1126 | | | | | | |
| 1146 | | | | | | |
| 1149 | | | | | | |
| 1221 | | | | | | |
| 1261 | | | | | | |
| 1267 | | | | | | |
| 1422 | | | | | | |
| 1445 | | | | | | |
| 1450 | | | | | | |
| 1454 | | | | | | |
| 1457 | | | | | | |
| 1459 | | | | | | |
| 1461 | | | | | | |
| 1565 | | | | | | |
| 1567 | | | | | | |
| 1650 | | | | | | |
| 05T | | | | | | |
| 06T | | | | | | |
| 07T | | | | | | |
| 08T | | | | | | |
| 10T | | | | | | |
| 11T | | | | | | |
| 12T | | | | | | |
| 13T | | | | | | |
| 15T | | | | | | |
| 16T | | | | | | |
| 17T | | | | | | |
| 18T | | | | | | |
| 20T | | | | | | |
| 22T | | | | | | |
| Sensitivity: | 0.7 | 0.7 | 0.633 | 0.6 | 0.567 | 0.467 |
| Total Sensitivity | 0.9 | | | | | |

| Adjacent mucosa | mgmiR 124-1 | mgmiR 124-2 | mgmiR 124-3 | mgmiR 137 | mgmiR 9-1 | mgmiR 9-3 |
|---|---|---|---|---|---|---|
| 1262 | | | | | | |
| 1266 | | | | | | |
| 1423 | | | | | | |
| 1446 | | | | | | |
| 1451 | | | | | | |
| 1455 | | | | | | |
| 1458 | | | | | | |
| 1460 | | | | | | |
| 1462 | | | | | | |
| 1566 | | | | | | |
| 1568 | | | | | | |
| 1651 | | | | | | |
| 05N | | | | | | |
| 06N | | | | | | |
| 07N | | | | | | |
| 08N | | | | | | |
| 10N | | | | | | |
| 11N | | | | | | |
| 12N | | | | | | |
| 13N | | | | | | |
| 15N | | | | | | |
| 16N | | | | | | |
| 17N | | | | | | |
| 18N | | | | | | |
| 20N | | | | | | |
| 22N | | | | | | |
| Sensitivity | 0.154 | 0.038 | 0.231 | 0.038 | 0.115 | 0.038 |
| Total Sensitivity | 0.423 | | | | | |

| normal mucosa | mgmiR 124-1 | mgmiR 124-2 | mgmiR 124-3 | mgmiR 137 | mgmiR 9-1 | mgmiR 9-3 |
|---|---|---|---|---|---|---|
| 1182 | | | | | | |
| 1424 | | | | | | |
| 1708 | | | | | | |
| 1722 | | | | | | |
| 1731 | | | | | | |
| 1741 | | | | | | |
| 1759 | | | | | | |
| 1760 | | | | | | |
| Total Specificity | 1 | | | | | |

Saliva:

| | HPV Positive (8) | | HPV Negative (11) | |
|---|---|---|---|---|
| | Sensitivity | Specificity | Sensitivity | Specificity |
| 124-2 | 87.50% | 100.00% | 63.64% | 100.00% |
| 137 | 62.50% | 91.67% | 45.45% | 91.67% |
| 124-1 | 14.29% | 100.00% | 20.00% | 100.00% |
| 9-1 | 50.00% | 83.33% | 18.18% | 83.33% |
| 124-3 | 75.00% | 91.67% | 36.36% | 91.67% |
| Overall | 100.00% | 93.33% | 81.82% | 93.33% |

Tissue:

| | HPV Positive (8) | | HPV Negative (10) | |
|---|---|---|---|---|
| | Sensitivity | Specificity | Sensitivity | Specificity |
| 124-2 | 75.00% | 100.00% | 90.00% | 100.00% |
| 137 | 75.00% | 100.00% | 70.00% | 100.00% |
| 124-1 | 62.50% | 100.00% | 70.00% | 100.00% |
| 9-1 | 62.50% | 100.00% | 40.00% | 100.00% |
| 124-3 | 62.50% | 91.67% | 60.00% | 91.67% |
| Overall | 100.00% | 98.33% | 90.00% | 98.33% |

Figure 9

Saliva:

| | EGFR Positive (10) | | EGFR Negative (7) | |
|---|---|---|---|---|
| | Sensitivity | Specificity | Sensitivity | Specificity |
| 124-2 | 80.00% | 100.00% | 75.00% | 100.00% |
| 137 | 50.00% | 91.67% | 62.50% | 91.67% |
| 124-1 | 20.00% | 100.00% | 12.50% | 100.00% |
| 9-1 | 40.00% | 83.33% | 25.00% | 83.33% |
| 124-3 | 60.00% | 91.67% | 50.00% | 91.67% |
| Overall | 100.00% | 93.33% | 87.50% | 93.33% |

Tissue:

| | EGFR Positive (10) | | EGFR Negative (7) | |
|---|---|---|---|---|
| | Sensitivity | Specificity | Sensitivity | Specificity |
| 124-2 | 90.00% | 100.00% | 85.71% | 100.00% |
| 137 | 70.00% | 100.00% | 85.71% | 100.00% |
| 124-1 | 60.00% | 100.00% | 85.71% | 100.00% |
| 9-1 | 60.00% | 100.00% | 42.86% | 100.00% |
| 124-3 | 70.00% | 91.67% | 57.14% | 91.67% |
| Overall | 100.00% | 98.33% | 100.00% | 98.33% |

Figure 10

|  | Saliva | | Tissue | | Saliva | | Tissue | |
|---|---|---|---|---|---|---|---|---|
|  | Nasal Cavity (2) | | Nasal Cavity (2) | | Oral Cavity (6) | | Oral Cavity (6) | |
|  | Sensitivity | Specificity | Sensitivity | Specificity | Sensitivity | Specificity | Sensitivity | Specificity |
| 124-2 | 100.00% | 100.00% | 100.00% | 100.00% | 83.33% | 100.00% | 100.00% | 100.00% |
| 137 | 100.00% | 50.00% | 91.67% | 100.00% | 66.67% | 50.00% | 100.00% | 100.00% |
| 124-1 | 0.00% | 100.00% | 100.00% | 100.00% | 16.67% | 100.00% | 83.33% | 100.00% |
| 9-1 | 0.00% | 83.33% | 0.00% | 100.00% | 16.67% | 83.33% | 83.33% | 100.00% |
| 124-3 | 0.00% | 91.67% | 50.00% | 91.67% | 33.33% | 91.67% | 83.33% | 91.67% |
| Overall | 100.00% | 93.33% | 100.00% | 98.33% | 100.00% | 93.33% | 100.00% | 98.33% |

|  | Saliva | | Tissue | | Saliva | | Tissue | |
|---|---|---|---|---|---|---|---|---|
|  | Oropharynx (6) | | Oropharynx (6) | | Hypopharynx (2) | | Hypopharynx (2) | |
|  | Sensitivity | Specificity | Sensitivity | Specificity | Sensitivity | Specificity | Sensitivity | Specificity |
| 124-2 | 83.33% | 100.00% | 100.00% | 100.00% | 100.00% | 100.00% | 100.00% | 100.00% |
| 137 | 50.00% | 50.00% | 66.67% | 100.00% | 100.00% | 50.00% | 100.00% | 100.00% |
| 124-1 | 33.33% | 100.00% | 83.33% | 100.00% | 50.00% | 100.00% | 100.00% | 100.00% |
| 9-1 | 33.33% | 83.33% | 66.67% | 100.00% | 50.00% | 83.33% | 50.00% | 100.00% |
| 124-3 | 66.67% | 91.67% | 83.33% | 91.67% | 50.00% | 91.67% | 100.00% | 91.67% |
| Overall | 100.00% | 93.33% | 100.00% | 98.33% | 100.00% | 93.33% | 100.00% | 98.33% |

|  | Saliva | | Tissue | | Saliva | | Tissue | |
|---|---|---|---|---|---|---|---|---|
|  | Larynx (4) | | Larynx (4) | | Other (4) | | Other (2) | |
|  | Sensitivity | Specificity | Sensitivity | Specificity | Sensitivity | Specificity | Sensitivity | Specificity |
| 124-2 | 50.00% | 100.00% | 25.00% | 100.00% | 75.00% | 100.00% | 50.00% | 100.00% |
| 137 | 25.00% | 50.00% | 50.00% | 100.00% | 75.00% | 50.00% | 50.00% | 100.00% |
| 124-1 | 0.00% | 100.00% | 0.00% | 100.00% | 0.00% | 100.00% | 100.00% | 100.00% |
| 9-1 | 50.00% | 83.33% | 25.00% | 100.00% | 50.00% | 83.33% | 50.00% | 100.00% |
| 124-3 | 75.00% | 91.67% | 25.00% | 91.67% | 50.00% | 91.67% | 50.00% | 91.67% |
| Overall | 75.00% | 93.33% | 75.00% | 98.33% | 75.00% | 93.33% | 100.00% | 98.33% |

Figure 11

|  | Saliva | | Tissue | | Saliva | | Tissue | |
|---|---|---|---|---|---|---|---|---|
| Differentiation: | Poorly (6) | | Poorly (6) | | Poorly/Moderately (2) | | Poorly/Moderately (2) | |
|  | Sensitivity | Specificity | Sensitivity | Specificity | Sensitivity | Specificity | Sensitivity | Specificity |
| 124-2 | 100.00% | 100.00% | 83.33% | 100.00% | 100.00% | 100.00% | 100.00% | 100.00% |
| 137 | 100.00% | 91.67% | 66.67% | 100.00% | 50.00% | 91.67% | 100.00% | 100.00% |
| 124-1 | 16.67% | 100.00% | 100.00% | 100.00% | 50.00% | 100.00% | 100.00% | 100.00% |
| 9-1 | 50.00% | 83.33% | 50.00% | 100.00% | 0.00% | 83.33% | 100.00% | 100.00% |
| 124-3 | 50.00% | 91.67% | 66.67% | 91.67% | 50.00% | 91.67% | 100.00% | 91.67% |
| Overall | 100.00% | 93.33% | 100.00% | 98.33% | 100.00% | 93.33% | 100.00% | 98.33% |

|  | Saliva | | Tissue | | Saliva | | Tissue | |
|---|---|---|---|---|---|---|---|---|
| Differentiation: | Moderately (10) | | Moderately (10) | | Moderately/Well (1) | | Moderately/Well (1) | |
|  | Sensitivity | Specificity | Sensitivity | Specificity | Sensitivity | Specificity | Sensitivity | Specificity |
| 124-2 | 70.00% | 100.00% | 80.00% | 100.00% | 100.00% | 100.00% | 100.00% | 100.00% |
| 137 | 50.00% | 91.67% | 60.00% | 100.00% | 0.00% | 91.67% | 100.00% | 100.00% |
| 124-1 | 20.00% | 100.00% | 50.00% | 100.00% | 0.00% | 100.00% | 100.00% | 100.00% |
| 9-1 | 40.00% | 83.33% | 50.00% | 100.00% | 0.00% | 83.33% | 100.00% | 100.00% |
| 124-3 | 60.00% | 91.67% | 60.00% | 91.67% | 0.00% | 91.67% | 100.00% | 91.67% |
| Overall | 90.00% | 93.33% | 90.00% | 98.33% | 100.00% | 93.33% | 100.00% | 98.33% |

|  | Saliva | | Tissue | |
|---|---|---|---|---|
| Differentiation: | Dysplasia (2) | | Dysplasia (2) | |
|  | Sensitivity | Specificity | Sensitivity | Specificity |
| 124-2 | 100.00% | 100.00% | 100.00% | 100.00% |
| 137 | 100.00% | 91.67% | 100.00% | 100.00% |
| 124-1 | 0.00% | 100.00% | 100.00% | 100.00% |
| 9-1 | 0.00% | 83.33% | 50.00% | 100.00% |
| 124-3 | 0.00% | 91.67% | 100.00% | 91.67% |
| Overall | 100.00% | 93.33% | 100.00% | 98.33% |

Figure 12

| SEQ ID | primer sequences of the qMS-PCR (mgmiR assay) | |
| --- | --- | --- |
| #1 | mgmir124-1F1 | GAGTTGCGGCGGGGAGGA |
| #2 | mgmir124-1R1 | CGACGCGTATACGTACGCACTAACAA |
| #3 | mgmir124-2F1 | TATTAGAGGGGTAATTAATTTGGATTTACGTCG |
| #4 | mgmir124-2R1 | ACGATACGTATACCTACGTATACATATACATAT |
| #5 | mgmiR124-3F1 | CGAAGACGTTTGAGCGTTCG |
| #6 | mgmiR124-3R1 | GAACGTCGAAACCAAAATCG |
| #7 | mgmiR137F1 | TAGCGGTAGCGGTAGTAGC |
| #8 | mgmiR137R1 | ACCCAAAAATACCCGTCACCG |
| #9 | mgmir9-1F1 | TTCGTTGACGGGCGATCGG |
| #10 | mgmir9-1R1 | ACTATCGCCGCCTCTTCCAC |
| #11 | mgmir9-3F1 | AGGTCGGTAGCGTCGGTGTT |
| #12 | mgmir9-3R1 | TAAACGAACGCCGTACCCGAA |

Sequence was generated from human ensemble database; human chromosome GRCH38.

SEQ ID: #13

Sequence of genomic loci encoding miR124-1 (reverse strand)

>chromosome 8: 9903388---9904472 (GRCh38)

CAGCCCCATTCTTGGCATTCACCGCGTGCCTTAATTGTATGGACATTTAAATCAAGGTCC
GCTGTGAACACGGAGAGAGAGGCCTTTCTCCTGAGGAAGGAAAGGAGGAAGGAAGGAAGG
AAAGGTGAAAGAAAGGAAGAGGGGTGGGTAGAAGATGGAATAAGAAAACCAGGAAAAAGA
AATAAAAAGCGGCGCGTGTGCGTGCGCACTGACAGCGGGGAGAGGGATGGGGGTGGGGAA
CGCCGGAGGAAGGGACCACAGCATCCTCCCCGCCGCAGCTCCCCAATCACACAGACAAT
GAGATAACAGCGACGTCTTCCAAAGGCTCTTTGTTCTCCCCATCCTTTCGCATCCAGGC
TTTTTCCTGCAAAGCGGAGGGGTGGAGGGATGGGGGTGTGGGTGGAAGTGGGAGACGGA
GGGGTGCCTCCCCGTGTTAATTACCCCGGCTCCCCTCGCCCCTTTCCCCGCGCCTCGCC
TCCCCTGCAGCTCCAGACAATGAAAAAACAACATCGACCCCACCTCGCCCCAGCGCAGCA
ACCCACCCACCCATGTCGCCCTCTGCTTCGCCCAGGAAACTGAAGGGGACTAGGAGGAGG
AAGAAGAGAGCGAAGGACAAGGAGAGCAGCGGGGACTCGGCAGCGGCAGCCGGGGCAGGG
CGCGCGGCCGCCGCCTCTTTACCTCCATCGCTGAGTGGGGCGCAGCCGGGCCGGGCGTG
CCGCAGGGGCGAGTTGCCGCGGTCCGGGGCTGGGACCTGGGGATTCAGCCTTCCGGAACT
CGCCTGCTGCAGTCCTCTCGCTCAGGTCCCAAGTGGTGGAGGGGGGAAAGGAAGAGAGAC
GAGAGAGAGAGACAGAGAGAGAGAGAGAGAGGAAGAAGAAGAAGAAGAAGAAAAA
AAACCATAAGAGCGAGGCCCATCTGGCCCCTCATCAGCTTTGTCAAGTCTTGCATACGCT
AAAATGCTAATGACCTAGATAGCTCATGCAAAATGCAGCAGGGAGGGCGGGAGCGAGGGA
GGTGGGAGGGAGGAAGAGAGAGGAGTGCAGGGGGGAGGGAGGGAGGAGAGGCGGAGGGAG
GGAGA

Figure 13

SEQ ID: #14

Sequence of genomic loci encoding miR124-2 (forward strand)

>chromosome 8:64378149---64379257 (GRCh38)

TCGACCACGCCGTAGGGGACGCCGTGAAAAGAGCCGTCGCGCCCGCTGCCTCCTGCCCGC
TGCGCAGAGGGCTCCGCCCGTAGAGGTCAACTTCCCTCACCCTTTTCTCTCTCCTGCTTG
CCCTCCCTCCGCCCGGCCCAGGCGCTTCCAGCCCCAGACTGTGGCCACTGGCTGAGGAGT
GCGAGTCGGCTGCGCTGCCCTGAGCCTAATCCCTCTTCCGGGCCCAGACCCGAGGTCCGC
GCTCCTGGGCAGTGGGGAAGCTTTAGTGAGCAGGCTTTTCTCTCCGCAGCAAACTTGTAG
CCAGACCAGATGGGCCGCCCAGCTCTCTCGGGACTAGGCAGGTGCGGATGAGTTAATTTT
TCCGCATTACAAAGAAAGATGACCCAGCCCGCCCTTGGACTCTCTTTTCCCAAAATCTCC
CAACCAAACCCGCGGTAACGTTATCAAAGGACACAGAGCCCAGGCATATCTGTGTGTTTA
TCTTACAGGCACACACGCATGGTTTTCTCTTTTATATGCTAGATTTCATCCCTGACAGCA
GAAATGATTGGCAATGGTTATGACGGAGAACATGCAATAGCGTGGTCCTTAAAAACCTG
CCATTCCTTACAAGTGCCTTAGAAAGGATTCAGGGCGAACCAACTGGGTTAATTGCATTC
AGTAAAATAACACGATTACAAAATTAGATCTGTACCAGAGGGGTAATTAACTTGGATCCA
CGCCGTCATTTGAAAACTAGATTTATAGGCTTATGTATGTTTTTAGGCGTGTGCTGTAAA
TGGCATGGAGATATATGCATATGTATACGCAGGCACACGCACCGTCTACACTTCCACGGA
ACAGACTAATTAACAGCGGCTCTGGCAGATGTGTCAGAGATGAGCAGAGACAGGAGCTGG
GCTTATGAGTTATGACTCTAGGGGTAGAGACTCAGAGCGGAGAGAGGGGATGGGCAGGG
AGAGAAGAGTGGTAATCGCAGTGGGTCTTATACTTTCCGGATCAAGATTAGAGGCTCTGC
TCTCCGTGTTCACAGCGGACCTTGATTTAATGTCATACAATTAAGGCACGCGGTGAATGC
CAAGAGCGGAGCCTACGGCTGCACTTGAA

SEQ ID: #15

Sequence of genomic loci encoding miR124-3 (forward strand)

>chromosome 20:63177500---63178586 (GRCh38)

CTCGGGGAGGCAGCGGCGGGGCCGGTGTCCGGGTGACGTCACCGCGCGCCCCAGTGATAA
TCGGCCGGTGCCGGAGCGGAGCGCGGATACGCGCGGAGGCAACGGCGACGGCGGCGGCGG
CGGCGGGCGCGGGGACAGTTGCATCGGGGCCGGGCCGGGCTAGCAGGAGCTGGGCGCCTG
CAGCGTGGACCCCGTGGACACTCGGCTCGCAGCCGGCCTGCGGCGCTCGGGGACTTGCCT
GGCTCCCTTCTCGGGGTTCCCGCGCCCTTCTCCGCCCAGGGCAGCAGCGCGCGGGGCCCC
CGGGAGCCGAAGAGCAGGCGGGAACTGGCGGCGGCGCGGGAGGCGCAGGGAGCGGAGGCG
GCAGCAGCGGCTCCCGCCGGGACTGGTAATTACGCTCGGGGCCGGGCCGGGGCGAGCCGG
GCAAGCGGCCTCTCTGGGTCTCCCCGTCTTTCTCTCCACGAACAGCTCGAGCGCCTTCTC
GCGGGCCCGCTGCGCGCGGAGAGGACGAGCTCGCTGGGTTGTAAAAGAGACGAGTTTTC
ATCTTTGAGCATCGAGATTCGTTCTTTTAACCGCATTCGGTGCGCGCTCCTGGGTCGGCA
CGGGCAGGGCGACGGCAGGGGAAGGCAGCTGCGGAGGAGCTCGCGCCGCCCAGTCGGAGC
GGTTCTGCGCCCCTCGGAGCCCCGCGGGAGGCGGCCGGGTGCGCACGCGCTCACCACCCC
CACCCCCGGAATCCGTCTTCGCGATTCCCGGGCGCCCCAGCTCCAGGAACGCCCGGAGGG
ACGCACTTGGGGGCCCACTCTCTGCCGCGGAAAGGGGAGAAGTGTGGGCTCCTCCGAGTC
GGGGGCGGACTGGGACAGCACAGTCGGCTGAGCGCAGCGCCCCGCCCTGCCCGCCACGC
GGCGAAGACGCCTGAGCGTTCGCGCCCCTCGGGCGAGGACCCCACGCAAGCCCGAGCCGG
TCCCGACCCTGGCCCCGACGCTCGCCGCCCGCCCCAGCCCTGAGGGCCCCTCTGCGTGTT
CACAGCGGACCTTGATTTAATGTCTATACAATTAAGGCACGCGGTGAATGCCAAGAGAGG
CGCCTCC

SEQ ID: #16

Sequence of genomic loci encoding miR137 (reverse strand)

>chromosome 1:98046070---98047171 (GRCh38)

TGCCGCTGGTACTCTCCTCGACTACGCGTATTCTTAAGCAATAACAACGTAATCCGTATT
ATCCACCCAAGAATACCCGTCACCGAAGAGAGTCAGAGGACCAAGCTGCCGCTGCCGCTG
CTACCGCTGCCGCTGCTACCGCTGCCGCTGCTACTGCCGCCGCCGCCGCCACCAGAACTC
TTGCTGCTCGCTGAGCCCGCCCCTGCCTGGGGATGGGCTGAGCTTGACCGGGACCATAAA
TCCATAACTCGATTTCCCTAAAGAAGGATCCAAAGCTGTGCTCGGCTGCTTCCTGCCCAA
ATCCAAATGGCCGCTCTATTTCCAATTCTGAAAGACAAATCACAAAATCAAATACTTAAC
ACAGAAGAGTGCTGTCTTTCCAGTGAGGAGGGAAGATGTGGCAAGGCTTTTTGGGCACAA
GTGGGAGTGACAAGTAACCTTCAGTTTACCTGGTGCTCTCCCAGTGCTTTCCTCTGCACT
TCTCTGCTTGGTACCCAGTCTGGTCTCGGCCAGTCCACTCTAGGTGGTATGATTGAGTGC
CATGGCGGCCAGAGAACCCTGTAAGAGACGTGAATAGTTACCCACACAAATACAAATATA
TTTGCCTAGACGGCTTTGGGAAGAAGTGAGGCTTAAATAAAGATAGGTCATGCATGGGTG
AAATTTTCAGTAGTGTGTTTTGGAAATGCACTTTTCTCAAGCCCAAGATCATGGAAAATA
AACACTCATTCAATTTACTACTTGAAATCAAATACTTATAGATGTACAAAAATAGGCGTC
TTTCCTTTGAAGGCCTTATAGCTATACAACATAATGATTTTTAAAGAAAAAAAAAGCTT
GAAGGCACACAGTAATTAAACCCATTTTCCATAGTGTCAAAACTCACTGAGTTGACAAGC
TGGTAGACTTTCTATGATTTAAGCATCATTTTATATCACTACAATGTTTAATTTCATAGC
ACACTTTTAAAATATATACTATAAATGCATTGCTGTACAGCTGTTGTGGACACCTCTACA
GAAAAACCTTTGAAGCTCTGTGTTCATAAATATTATTTTAAGAAGAAAAAGCCAATAAAA
ACTCATTTGCAAAGTGACTGTA

SEQ ID: #17

Sequence of genomic loci encoding miR9-1 (reverse strand)

>chromosome 1: 156420331---156421438 (GRCh38)

GCGCAGTGTATGGGGTTATTTTTACTTTCGGTTATCTAGCTTTATGAAGACTCCACACCA
CTCATACAGCTAGATAACCAAAGATAACAACCAACCCCGCCTCCTGGCTGCTGTCGCCGC
CTCTTCCACGCAGCCTCCCGGCCGCCGCCGCCGCCAGCACCTCCGCAGCTTCCCGGTCGC
CCGTCAGCGGGAGTAGGAGGGAAGGGACACGAGTGGAGTTGAGGGGGAGGGTGAAGAGAG
AAATGAAGTCCGAGACAAAACAACAACAAAAACCTCAGACACGGAGATACAGACACGACA
GAGACCGAAAAAGGCGTGGAAAGGACGCGATGACCCGTGGCGTCGAAGTCGGGGAGTTGA
CCCCGATCCAGACCCAAAAAGTTTCTGGTGCCCCATTTCCCGCTCTCCCATTCGGGCCAG
GAGCAGGAGTTCCGCTGGTCCCAGGTGGAAGGGACGCGCGGGCTTTTCGTGCCACCCGGG
AAGACCGCAGCGACCCAGGCAGAGGCCTCCCCAGCCTCGCCGGGTCTCCACTGCCCTTCT
CTGGAAGATCGAGGGCGCATCCGACAGCCAGAGCCCTGCCTTCGGCGGAGCCCGAGCCTG
GCGCGGGATGGAAATGGGGAGCCGCGGTGCCGGCCCGGCCACGTCGCCAACTCAGAAAGG
CGTTGGAAGCGAAGCGGAGCCCTTGTGGGGAAAGAGCCGGATTCAAGAGGCCGACTAAA
AGGGGAAATGGGCAGCCAAACCCCGGAGGTAAAAACCCCAGAGATGTCCTAATAGGAAGC
AGGGAAATCCCGGCGACCCAAAGAGAGGAAAGGCTGTGGGGGCGGGTGGGGGCGACC
CAGAGACTCCCAAGCGAGTCTCTCAAGGAGAGAAGGAAACAGCAGAGACCCCACCCGGGA
AGAGATCCGGGAGAGTACCCATGAGAGGGCGGAGGGGAGGAAAGCAGAGGGCGACAGGG
CAGGTGACCAGAGTCCCAGGCCCTGCAGAGCCCCGGATAAACGGCTTTGTTCAAAGAGGA
CCAGAGATCACCCAGGGTTGTGAAAATGGCCGGGGGTTCGAGGCGAGCGGTGCTCTAGGG
GTGGGAAAGGGGTGCGATCAGGAACGGG

Figure 13 (cont.)

SEQ ID: #18

Sequence of genomic loci encoding miR9-3 (forward strand)

>chromosome 15:89367017---89368106 (GRCh38)

AATCGGTTTTACACTCCTAGTGTGTCTAGGAACCGAGAGAGAGAAGGGACCTAGCAGCTT
GGTACTCAGGGCCCAGGCCAGGGCCTCGCCCAAGTGGAGCATAGCTGAGGAACCTCTGAG
TGCCAGGTGTTATGGGTGGGACACCGACCTGCGCTCACCGGGACACTTAATTCTTCCTCC
AATCCCTGGTCTCTGCCGCGTGGGCTAGATCTACTGCAAGTGCTGGGCATGGGGAAAGGA
AGAGAGAAGTTAAAGGTGAAATGGCTTCTGCTCTCGGCCTCTCCGTGAGCGCTCTCGGCC
CTCCTGTGGAGATCGCCACGTCCTATCACACGCGTCCCTAAACCTTGTCACTCGAGCATT
CTTGTCTCCCAAACTCTGATGGTCCGCAGTGGGTACTGGGCTCCCTGGGCCCTGGGAGGA
AGACGGAGGAGTTTGGGTGAAAGATCAGACGGTGCGCAGCCCTGAGGCTTCTGAGGGCAG
AGGGTGCGCTTCCTTGCCCTCGGGGCGGGGAAGCCGTGAACGCCGAGGCCATTGTAAGGC
TGGGTGGTGCGGAGCGCGGGAAGGGGGCTGGGATTTGAATGGGAGCCTGTGATTGGCCGA
TCCCTGGACTGACGTCACTTCCCCGCGGGGCGATTAGCCTGCGAGAGGAGGGCCGGCGGT
CCAGTGCGCTGGGGGCGGCCGGGGCGCTCGAGGCTCTCTAAGCGCTCCGCGCGGGTGCCC
TACGTGAGCCCCGGGACGCCGTCGAGGCAGGCCGGCAGCGCCGGTGCCAGGACGCACGGA
ACGGGGAGCAGGGGAGAAATGCGCCGGGAGGGCGAGGGAGGAAGGGAACTGGGCGGGGGC
TGCGGGCCTAGGTGGCGGGAGTCAGCGTGTGCGTGTGTCTGTCCATCCCCTCTGGCTCTC
CGCGTGCGCCCCAGGATCCGGGCACGGCGTCCGCTCAGGCTCCCGCGCTCGGCAGGCAGC
AGCACGTGGAGCCCACGGCGCGGCAGCGGCACTGGCTAAGGGAGGCCCGTTTCTCTCTTT
GGTTATCTAGCTGTATGAGTGCCACAGAGCCGTCATAAAGCTAGATAACCGAAAGTAGAA
ATGATTCTCA

Figure 13 (cont.)

SEQUENCE LISTING

```
Sequence total quantity: 15
SEQ ID NO: 1            moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 1
gagttgcggc ggggagga                                                   18

SEQ ID NO: 2            moltype = DNA  length = 26
FEATURE                 Location/Qualifiers
misc_feature            1..26
                        note = synthetic
```

```
                            source             1..26
                                               mol_type = other DNA
                                               organism = synthetic construct
SEQUENCE: 2
cgacgcgtat acgtacgcac taacaa                                                    26

SEQ ID NO: 3               moltype = DNA   length = 33
FEATURE                    Location/Qualifiers
misc_feature               1..33
                           note = synthetic
source                     1..33
                           mol_type = other DNA
                           organism = synthetic construct
SEQUENCE: 3
tattagaggg gtaattaatt tggatttacg tcg                                             33

SEQ ID NO: 4               moltype = DNA   length = 33
FEATURE                    Location/Qualifiers
misc_feature               1..33
                           note = synthetic
source                     1..33
                           mol_type = other DNA
                           organism = synthetic construct
SEQUENCE: 4
acgatacgta tacctacgta tacatataca tat                                             33

SEQ ID NO: 5               moltype = DNA   length = 20
FEATURE                    Location/Qualifiers
misc_feature               1..20
                           note = synthetic
source                     1..20
                           mol_type = other DNA
                           organism = synthetic construct
SEQUENCE: 5
cgaagacgtt tgagcgttcg                                                            20

SEQ ID NO: 6               moltype = DNA   length = 20
FEATURE                    Location/Qualifiers
misc_feature               1..20
                           note = synthetic
source                     1..20
                           mol_type = other DNA
                           organism = synthetic construct
SEQUENCE: 6
gaacgtcgaa accaaaatcg                                                            20

SEQ ID NO: 7               moltype = DNA   length = 19
FEATURE                    Location/Qualifiers
misc_feature               1..19
                           note = synthetic
source                     1..19
                           mol_type = other DNA
                           organism = synthetic construct
SEQUENCE: 7
tagcggtagc ggtagtagc                                                             19

SEQ ID NO: 8               moltype = DNA   length = 21
FEATURE                    Location/Qualifiers
misc_feature               1..21
                           note = synthetic
source                     1..21
                           mol_type = other DNA
                           organism = synthetic construct
SEQUENCE: 8
acccaaaaat acccgtcacc g                                                          21

SEQ ID NO: 9               moltype = DNA   length = 19
FEATURE                    Location/Qualifiers
misc_feature               1..19
                           note = synthetic
source                     1..19
                           mol_type = other DNA
                           organism = synthetic construct
SEQUENCE: 9
ttcgttgacg ggcgatcgg                                                             19

SEQ ID NO: 10              moltype = DNA   length = 20
FEATURE                    Location/Qualifiers
misc_feature               1..20
```

-continued

```
                        note = synthetic
source                  1..20
                        mol_type = other DNA
                        organism = synthetic construct
SEQUENCE: 10
actatcgccg cctcttccac                                                 20

SEQ ID NO: 11           moltype = DNA  length = 1085
FEATURE                 Location/Qualifiers
source                  1..1085
                        mol_type = genomic DNA
                        organism = Homo sapiens
SEQUENCE: 11
cagccccatt cttggcattc accgcgtgcc ttaattgtat ggacatttaa atcaaggtcc     60
gctgtgaaca cggagagaga ggcctttctc ctgaggaagg aaaggaggaa ggaaggaagg    120
aaaggtgaaa gaaaggaaga ggggtgggta gaagatggaa taagaaaacc aggaaaaaga   180
aataaaaagc ggcgcgtgtg cgtgcgcact gacagcgggg agagggatgg gggtggggaa   240
cgccggagga agggaccaca gcatcctccc cgccgcagct cccccaatca cagacacaat   300
gagataacag cgacgtcttc caaaggctct ttgttctccc ccatcctttc gcatccaggc   360
ttttttcctgc aaagcggagg gggtggaggg atggggtgt gggtggaagt gggagacgga   420
ggggtgcctc cccgtgtta attacccgg ctcccctcgc ccctttcccc gcgcctcgcc     480
tcccctgcag ctccagacaa tgaaaaaaca acatcgaccc cacctcgccc cagcgcaggc   540
acccacccac ccatgtcgcc ctctgcttcg cccaggaaac tgaagggac taggaggagg    600
aagaagagag cgaaggacaa ggagagcagc gggactcgg cagcggcagc cggggcaggg    660
cgcgcggcgc ccgcctcttt acctccatcg ctgagtgggg gcgcagccgg gccgggcgtg   720
ccgcagggc gagttgccgc ggtccgggc tgggacctga ggattcagcc ttccggaact    780
cgcctgctgc agtcctctcg ctcaggtccc aagtggtgga ggggggaaag gaagagagac   840
gagagagaga gagacagaga gagagagaga gaggaagaa agaagaagaa gaagaaaaaa    900
aaaccataag agcgaggccc atctggcccc tcatcagctt tgtcaagtct tgcatacgct   960
aaaatgctaa tgacctagat agctcatgca aaatgcagca gggagggcgg gagcgaggga  1020
ggtgggaggg aggaagagag aggagtgcag ggggagggga gggaggagag gcggagggag   1080
ggaga                                                              1085

SEQ ID NO: 12           moltype = DNA  length = 1109
FEATURE                 Location/Qualifiers
source                  1..1109
                        mol_type = genomic DNA
                        organism = Homo sapiens
SEQUENCE: 12
tcgaccacgc cgtaggggac gccgtgaaaa gagccgtcgc gccgctgcc tcctgcccgc     60
tgcgcagagg gctccgcccg tagggtcaa cttccctcac ccttttctct ctcctgcttg    120
ccctccctcc gccggccca ggcgcttcca gccccagact gtggccactg ctgaggagt     180
gcgagtcggc tgcgctgccc tgagcctaat ccctcttccg ggcccagacc cgaggtccgc   240
gctcctgggc agtggggaag ctttagtgag caggcttttc tctccgcagc aaacttgtag   300
ccagaccaga tgggccgccc agctctctcg ggactaggca ggtgcggatg agttaatttt   360
tccgcattac aaagaaagat gacccagccc gcccttggac tctcttttcc caaatctctc   420
caaccaaacc cgcggtaacg ttatcaaagg acacagagcc caggcatatc tgtgtgttta   480
tcttacaggc acacacgcat ggttttctct tttatatgct agatttcatc cctgacagca   540
gaaaatgatt ggcaatggtt atgacggaga acatgcaata gcgtggtcct taaaaacctg   600
ccattcctta caagtgcctt agaaaggatt cagggcgaac caactgggtt aattgcattc   660
agtaaaataa cacgattaca aaattagatc tgtaccagag gggtaattaa cttggatcca   720
cgccgtcatt tgaaaactag atttataggc ttatgtatgt ttttaggcgt gtgctgtaaa   780
tggcatggag atatatgcat atgtatacgc aggcacacgc accgtctaca cttccacgga   840
acagactaat taacagcggc tctggcagat gtgtcagaga tgagcagaga caggagctgg   900
gcttatgagt tatgactcta ggggtagaga ctcagagcgg agagaggggg atgggcaggg   960
agagaagagt ggtaatcgca gtgggtctta tactttccgg atcaagatta gaggctctgc  1020
tctccgtgtt cacagcggac cttgatttaa tgtcatacaa ttaaggcacg cggtgaatgc   1080
caagagcgga gcctacggct gcacttgaa                                    1109

SEQ ID NO: 13           moltype = DNA  length = 1087
FEATURE                 Location/Qualifiers
source                  1..1087
                        mol_type = genomic DNA
                        organism = Homo sapiens
SEQUENCE: 13
ctcggggagg cagcggcggg gccggtgtcc gggtgacgtc accgcgcgcc ccagtgataa     60
tcggccggtg ccggagcgga gcgcggatac gcgcggaggc aacggcgacg gcggcggcg    120
cggcgggcgc ggggacagtt gcatcggggc cgggccgggc tagcaggagc tgggcgcctg   180
cagcgtggac cccgtggaca ctcggctcgc agccggcctg ccggcgctcg ggacttgcct   240
ggctcccttc tcggggttcc cgcgcccttc tccgcccagg gcagcagcgc gcggggcccc   300
cgggagccga agagcaggcg ggaactggcg gcggcgcggg aggcgcaggg agcggaggcg   360
gcagcagcgg ctcccgccgg gactggtaat tacgctcggg gccgggccgg ggcgagccgg   420
gcaagcggcc tctctgggtc tccccgtctt tctctccacg aacagctcga gcgccttctc   480
gcgggcgctc tgcgcgggca gaggacgagc tcgctgggtt gtaaaaagag acgagttttc   540
atctttgagc atcgagattc gttctttaa ccgcattcgg tgcgcgctcc tgggtcggca    600
cgggcagggc gacggcaggg gaaggcagct cggaggagc tcgcgccgcc cagtcggagc    660
ggttctgcgc ccctcggagc cccgcgggag cggccgggt gcgcacgcgc tcaccacccc    720
cacccccgga atcgtcttc gcgattcccg ggcgcccag ctccaggaac gcccggaggg     780
acgcacttgg gggcccactc tctgccgcgg aaagggggaga agtgtgggct cctccgagtc   840
```

```
                                    -continued
ggggcggac tgggacagca cagtcggctg agcgcagcgc ccccgccctg cccgccacgc    900
ggcgaagacg cctgagcgtt cgcgcccctc gggcgaggac cccacgcaag cccgagccgg    960
tcccgaccct ggccccgacg ctcgccgccc gccccagccc tgagggcccc tctgcgtgtt   1020
cacagcggac cttgatttaa tgtctataca attaaggcac gcggtgaatg ccaagagagg   1080
cgcctcc                                                             1087

SEQ ID NO: 14           moltype = DNA  length = 1102
FEATURE                 Location/Qualifiers
source                  1..1102
                        mol_type = genomic DNA
                        organism = Homo sapiens
SEQUENCE: 14
tgccgctggt actctcctcg actacgcgta ttcttaagca ataacaacgt aatccgtatt     60
atccacccaa gaatacccgt caccgaagag agtcagagga ccaagctgcc gctgccgctg    120
ctaccgctgc cgctgctacc gctgccgctg ctactgccgc cgccgccgcc accagaactc    180
ttgctgctcg ctgagcccgc ccctgcctgg ggatgggctg agcttgaccg ggaccataaa    240
tccataactc gatttcccta aagaaggatc caaagctgtg ctcggctgct tcctgcccaa    300
atccaaatgg ccgctctatt tccaattctg aaagacaaat cacaaaatca aatacttaac    360
acagaagagt gctgtctttc cagtgaggag ggaagatgtg gcaaggcttt ttgggcacaa    420
gtgggagtga caagtaacct tcagtttacc tggtgctctc ccagtgcttt cctctgcact    480
tctctgcttg gtacccagtc tggtctcggc cagtccactc taggtggtat gattgagtgc    540
catggcggcc agagaaccct gtaagagacg tgaatagtta cccacacaaa tacaaatata    600
tttgcctaga cggctttggg aagaagtgag gcttaaataa agataggtca tgcatgggtg    660
aaattttcag tagtgtgttt tggaaatgca cttttctcaa gcccaagatc atggaaaata    720
aacactcatt caatttacta cttgaaatca aatacttata gatgtacaaa aataggcgtc    780
tttcctttga aggccttata gctatacaac ataatgattt ttaaagaaaa aaaaaagctt    840
gaaggcacac agtaattaaa cccattttcc atagtgtcaa aactcactga gttgacaagc    900
tggtagactt tctatgattt aagcatcatt ttatatcact acaatgttta atttcatagc    960
acactttttaa aatatatact ataaatgcat tgctgtacag ctgttgtgga cacctctaca   1020
gaaaaacctt tgaagctctg tgttcataaa tattatttta agaagaaaaa gccaataaaa    1080
actcatttgc aaagtgactg ta                                            1102

SEQ ID NO: 15           moltype = DNA  length = 1108
FEATURE                 Location/Qualifiers
source                  1..1108
                        mol_type = genomic DNA
                        organism = Homo sapiens
SEQUENCE: 15
gcgcagtgta tggggttatt tttactttcg gttatctagc tttatgaaga ctccacacca     60
ctcatacagc tagataacca aagataacaa ccaaccccgc ctcctggctg ctgtcgccgc    120
ctcttccacg cagcctcccg gccgcgccgc ccgccagcac ctccgcagct tcccggtcgc    180
ccgtcagcgc gagtaggagg gaagggacac gagtggagtt gaggggagg gtgaagagag     240
aaatgaagtc cgagacaaaa caacaacaaa aacctcagac acggagatac agacacgaca    300
gagaccgaaa aaggcgtgga aaggacgcga tgacccgtgg cgtcgaagtc ggggagttga    360
ccccgatcca gacccaaaaa gtttctggtg ccccattcc cgctctccca ttcgggccag     420
gagcaggagt tccgctggtc ccaggtgaa gggacgcgcg ggcttttcgt gccacccggg     480
aagaccgcag cgacccaggc agaggcctcc ccagcctcgc cgggtctcca ctgcccttct    540
ctggaagatc gagggcgcat ccgacagcca gagccctgcc ttcggcggag cccgagcctg    600
gcgcgggatg gaaatgggga gccgcggtgc cggcccggcc acgtcgccaa ctcagaaagg    660
cgttggaagc gaagcggagc ccttgtgggg gaaagagccg gattcaagag gccgactaaa    720
agggggaaatg ggcagccaaa ccccggaggt aaaaacccca gagatgtcct aataggaagc    780
agggaaatcc cggcgaccca aagagagagg aaaggctgtg gggggcgggt ggggcgacc     840
cagagactcc caagcgagtc tctcaaggag agaaggaaac agcagagacc ccacccggga    900
agagatccgg gagagtaccc atgagagggg cggagggag gaaagcagag ggcgacaggg    960
caggtgacca gagtcccagg ccctgcagag ccccggataa acggctttgt tcaaagagga   1020
ccagagatca cccaggggttg tgaaaatggc cggggggttcg aggcgagcgg tgctctaggg   1080
gtgggaaagg ggtgcgatca ggaacggg                                     1108
```

BIOMARKERS FOR HEAD AND NECK CANCER AND METHODS OF THEIR USE

RELATED APPLICATIONS

This application is a divisional of U.S. patent application Ser. No. 16/857,767, filed Apr. 24, 2020, which is a divisional of U.S. patent application Ser. No. 15/519,758, filed Apr. 17, 2017, now U.S. Pat. No. 10,640,831, issued May 5, 2020, which is a national phase entry under 35 U.S.C. § 371 of PCT/US15/55958 filed on Oct. 16, 2015, which claims priority to U.S. Provisional Patent Application No. 62/065,122, filed Oct. 17, 2014, which is incorporated by reference into the present application in its entirety and for all purposes.

BACKGROUND

Field of the Invention

The instant disclosure relates to detection and treatment of cancers. More particularly, it relates to the use of biomarkers for detecting cancers.

Description of Related Art

Head and neck squamous cell carcinoma (HNSCC) represents approximately 90% of all head and neck cancer and 5% of all malignancies. See Jemal et al. (2009) and Worshem et al. (2013). Oral cavity and pharynx cancers alone were the eighth most common cancer among males in the United States in 2008, and HNSCC was seen in more than 48,000 new patients in 2009 in the United States (Jemal et al.). HNSCC has also seen an increasing rate of prevalence over the past 30 years. See Worsham et al. (2013). Despite the advancements in medical and cancer therapy, the survival rates for patients with HNSCC have been fairly stagnant. See Siegel et al. (2013). This is in stark contrast to the increase in survival rates of many other cancers recently. One of the main reasons for the poor prognosis of HNSCC is that more than half of HNSCC patients have advanced to either locoregional or metastatic stages of the disease at the time of diagnosis. Therefore, early detection may be one key to improving survival rates in the future.

The discovery of microRNA (miRNA) in 1993 was one of the major events in molecular biology. See Lee et al. (1993). miRNAs are non-coding RNAs that are approximately 18-25 nucleotides in length. These molecules appear to be evolutionary conserved and instead of being translated into proteins, their main role is in gene regulation. Over the past twenty years, multiple studies have demonstrated that miRNAs serve important roles and affect fundamental cell processes, such as cellular development, differentiation, proliferation, survival and death. Ambros et al. (2004).

Over a thousand miRNAs have been discovered in the human genome with research demonstrating that one miRNA family on average affects approximately ~500 genes. See e.g., Lewis et al. (2003); Krek et al. (2005), Betel et al. (2008), and Friedman et al. (2009). Because of this prominent regulatory role on cellular genomics, researchers have investigated whether altered miRNAs play a role in tumorigenesis. Interestingly, studies have shown that miRNA may play a role in tumorigenesis in human neoplasia having distinctive miRNA expression signatures. Furthermore, miRNAs appear to have both tumor suppressor and oncogenic roles in tumorigenesis. With this discovery, extensive research has been focused on the possibility of miRNA as a potential target for cancer diagnosis and therapy. See e.g., Garzon et al. (2010). Another significant development in genetic research has been the increased understanding of epigenetics. Epigenetics is the study of heritable changes in gene activity that are not caused by alterations in the actual DNA. Probably the best known and scientifically established epigenetic process is DNA methylation. The addition of a methyl group to the DNA promoter region especially of the CpG-rich sequences of a specific gene has been shown to be a strong repressor of transcription equivalent to an actual mutation or deletion of the gene. In the last 15 years or so, epigenetics has been shown to play a significant role in the development of cancer. Specifically, hypermethylation of critical tumor suppressor genes has been revealed in many cancers, including HNSCC. See Worsham et al. (2013).

The majority of HNSCC affects the mucosal surface of the upper aerodigestive tract, which also includes esophageal cancer and lung cancer. To date, it still remains unanswered whether specific epigenetic changes could be used as a diagnostic tool for HNSCC.

SUMMARY

The present disclosure advances the art by providing methods for early detection of certain types of cancer. More particularly, disclosed here is a diagnostic panel of methylated genomic loci encoding microRNA (mgmiR) markers that demonstrated 90% sensitivity and 100% specificity in the detection of head and neck squamous cell carcinoma (HNSCC). These results represent the first use of quantitative MS-PCR for the detection of methylation level using mgmiR markers. In addition, this panel demonstrated the ability to detect hypermethylation in the adjacent mucosa of cancer patients, suggesting its utility in early detection. This panel is also capable of detecting cancer by using saliva, blood and fine-needle aspiration (FNA) tissue samples, among others.

In one embodiment, a method is disclosed for detecting cancer in a subject, which may include (a) measuring methylation level of at least one genomic locus encoding at least one microRNA selected from the group consisting of miR124-1, 124-2, 124-3, 137, 9-1 and 9-3, and (b) comparing the methylation level obtained from the subject with that of a corresponding genomic locus encoding the same microRNA from an individual known to be free from the cancer (the latter also being referred to as "base methylation level" or "base level" in this disclosure). The disclosed method may further include providing a diagnosis where a significantly higher methylation level of the DNA fragment in the subject as compared to the base methylation level is indicative of cancer or pre-cancer.

For purpose of this disclosure, the term "significantly higher" may mean at least 20%, 40%, 50%, 80%, 100%, 150%, 200% or even higher.

In another embodiment, a method for detecting cancer may include: (a) preparing a DNA extract from a tissue or a body fluid of the subject, where the DNA extract contains at least one first DNA fragment encompassing at least one genomic locus encoding at least one microRNA selected from the group consisting of miR124-1, 124-2, 124-3, 137, 9-1 and 9-3, (b) generating a second DNA fragment by polymerase chain reaction (PCR) using as a template the first DNA fragment and using as primers oligonucleotides specific to methylated DNA, (c) measuring the level of the second DNA fragment generated in step (b), and (d) comparing the level of the second DNA fragment with a base level, where a higher level of the second DNA fragment as compared to the base level is indicative of cancer or pre-cancer. In one aspect, the base level is the level of a corresponding DNA fragment generated by the same manner from the same tissue or body fluid of an individual known to be free from the cancer.

In another embodiment, the primers used for the qMS-PCR are primer pairs selected from the group consisting of SEQ ID Nos. 1-12. "F" indicates forward primer, "R" indicates reverse primer.

In one aspect, the disclosed methods may be suitable with or without modification for early detection of cancer (or pre-cancer). Examples of cancer may include but are not limited to head and neck squamous cell carcinoma (HNSCC), esophageal cancer, lung cancer, cervical cancer, breast cancer, colon cancer, rectal cancer, stomach cancer, pancreas cancer, liver cancer, gallbladder cancer, bile duct cancer, small intestine cancer, urinary tract cancer, female genital tract cancer, male genital tract cancer, endocrine gland cancer, skin cancer, hemangiomas, melanomas, sarcomas, brain tumor, nerve cancer, eye tumor, meninges cancer, or solid tumors from hematopoietic malignancies, among others.

In another embodiment, the at least one microRNA or the DNA fragment encoding the at least one microRNA may be isolated from a tissue or body fluid selected from the group consisting of a head tissue, a neck tissue, mouth swap, nose swap, saliva, sputum, blood, serum, Cerebrospinal fluid (CSF), urine, FNA tissue, other body fluids, or combination thereof The six genomic loci encoding microRNAs (also referred to as "mgmiRs" markers) may also be used as a panel, where at least one, two, three, four, five or all six need to show significantly higher level of methylation in the subject as compared to the base level before a positive call of cancer or pre-cancer is made.

In another embodiment, the base level may be a preset value established by averaging the levels obtained from two or more individuals known to be free from the cancer. By way of example, preset values are used in the Examples of the present disclosure but may be modified by one of skills in the art.

In another embodiment, a method is disclosed for detecting cancer in a subject, which may include (a) measuring the level of at least one microRNA in a tissue or body fluid isolated from the subject, wherein at least one microRNA is selected from the group consisting of miR124-1, 124-2, 124-3, 137, 9-1 and 9-3, and (b) comparing the level of the at least one microRNA with a base level, said base level being the level of the same microRNA from the same tissue or body fluid of an individual known to be free from the cancer, where a significantly lower level of the at least one microRNA in the subject as compared to the base level is indicative of cancer or pre-cancer.

BRIEF DESCRIPTION OF THE DRAWINGS

FIG. 2 shows the "Heat map" of the mgmiR biomarkers on examining HNSCC patients' tissues and control tissues

FIG. 8 shows the "HeatMap" of comparing the mgmiR biomarkers between tissues and saliva from same HNSCC patients, or control patients.

FIG. 9 shows the correlation between mgmiR biomarkers and HPV status.

FIG. 10 shows the correlation between mgmiR biomarkers and EGFR status.

FIG. 11 shows the correlation between mgmiR biomarkers and anatomic sites.

FIG. 12 shows the correlation between mgmiR biomarkers and pathological status.

FIG. 13 shows the sequence of primers used for the qMS-PCR (SEQ ID NOs. 1-12) and the sequences of the genomic loci encoding miR124-1, 124-2, 124-3, 137, 9-1 and 9-3 (SEQ ID NOs. 13-18).

DETAILED DESCRIPTION

Figure 1:
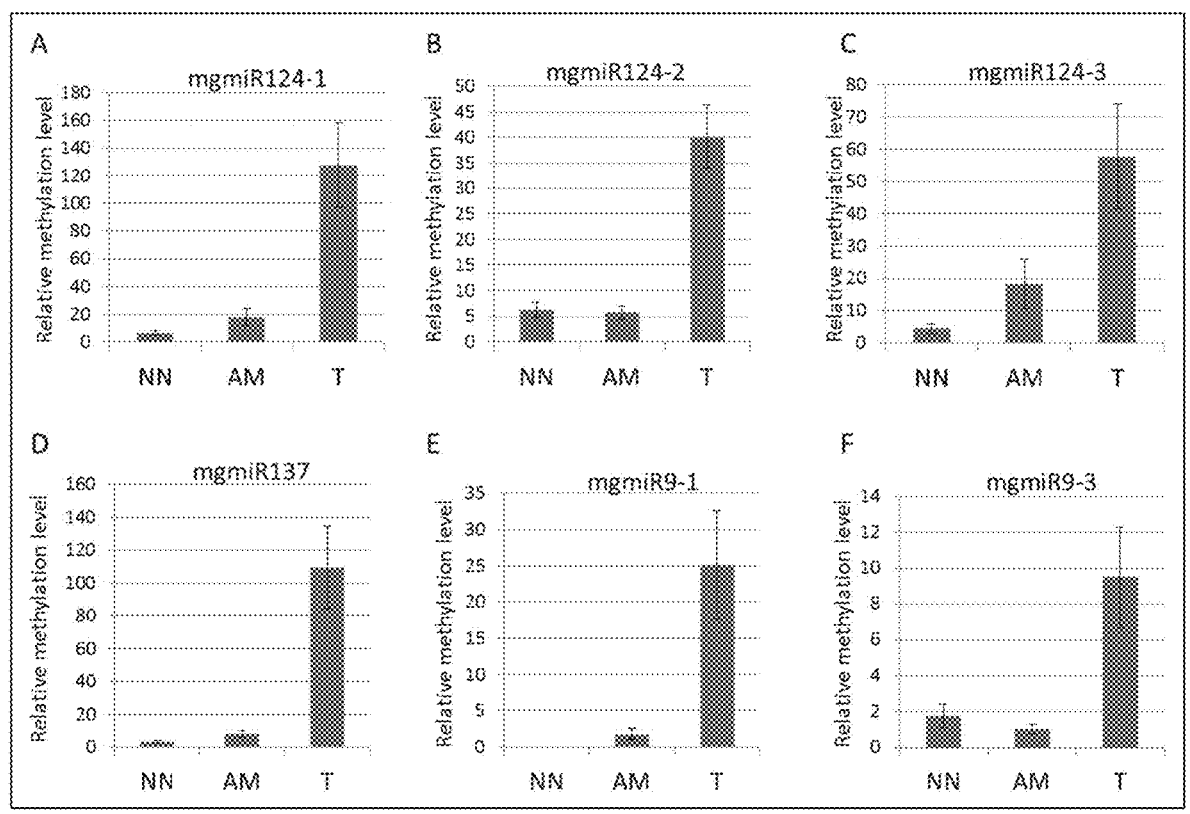
FIG. 1 shows the relative methylation level measured by individual mgmiR markers. NN-normal buccal mucosa from a cancer-free individual, AM-adjacent mucosa from an HNSCC patient, T-tumor tissue from a HNSCC patient.
Figure 3A:
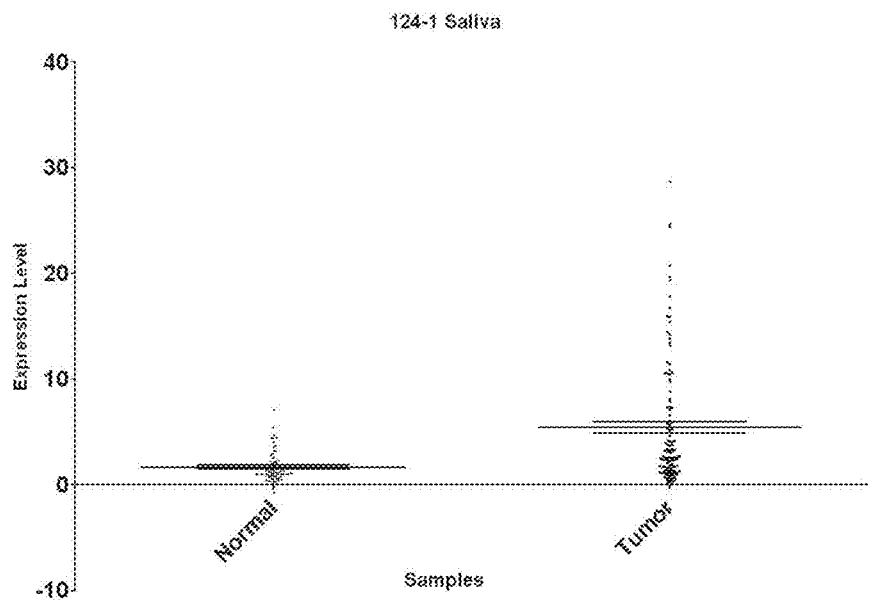
FIG. 3A shows qMS-PCR results that reveal the overall relative methylation level of both the control and subject samples as well as the methylation level of each patient's saliva sample for marker mgmiR124-1.
Figure 3B:
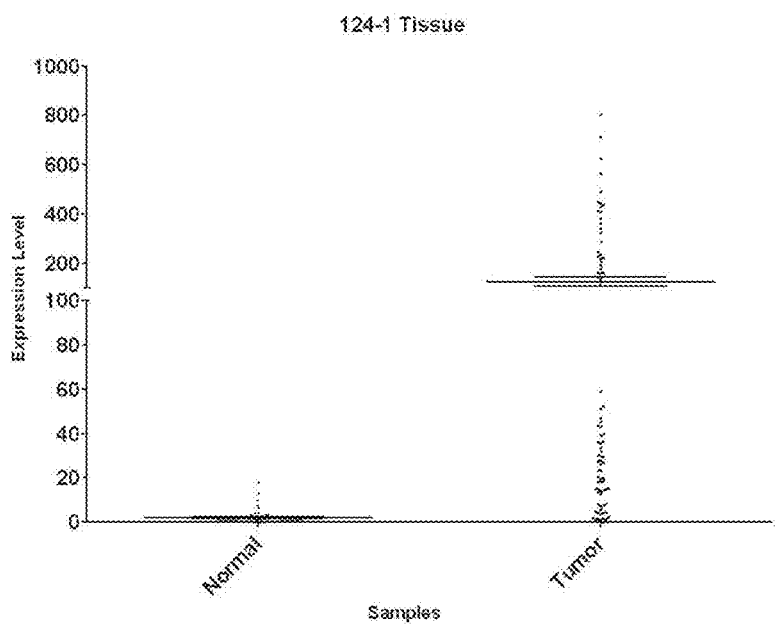
FIG. 3B shows qMS-PCR results that reveal the overall relative methylation level of both the control and subject samples as well as the methylation level of each patient's tumor sample for marker mgmiR124-1.
Figure 4A:
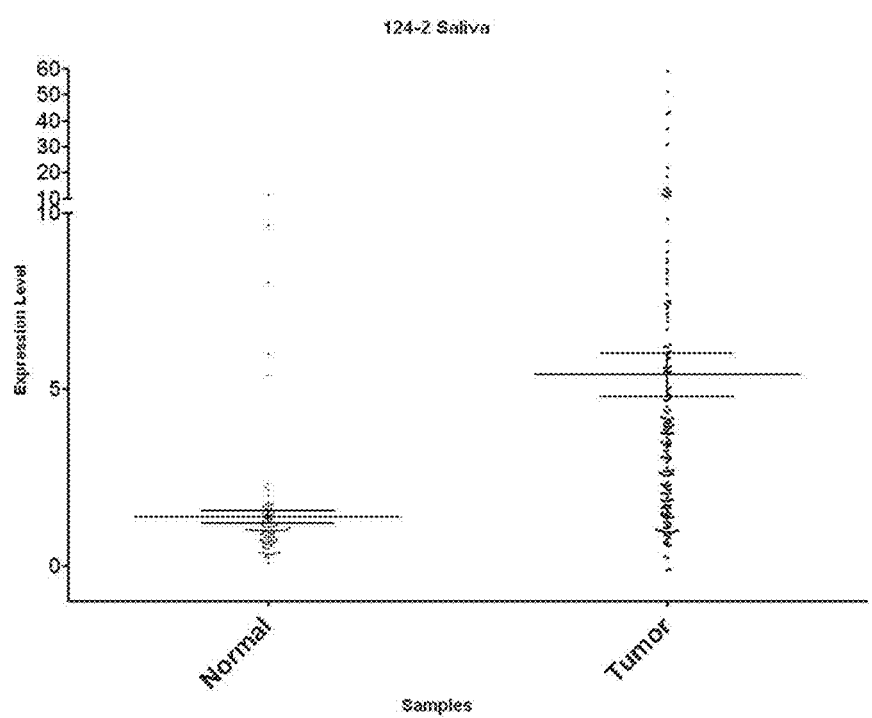
FIG. 4A shows qMS-PCR results that reveal the overall relative methylation level of both the control and subject samples as well as the methylation level of each patient's saliva sample for marker mgmiR124-2.
Figure 4B:
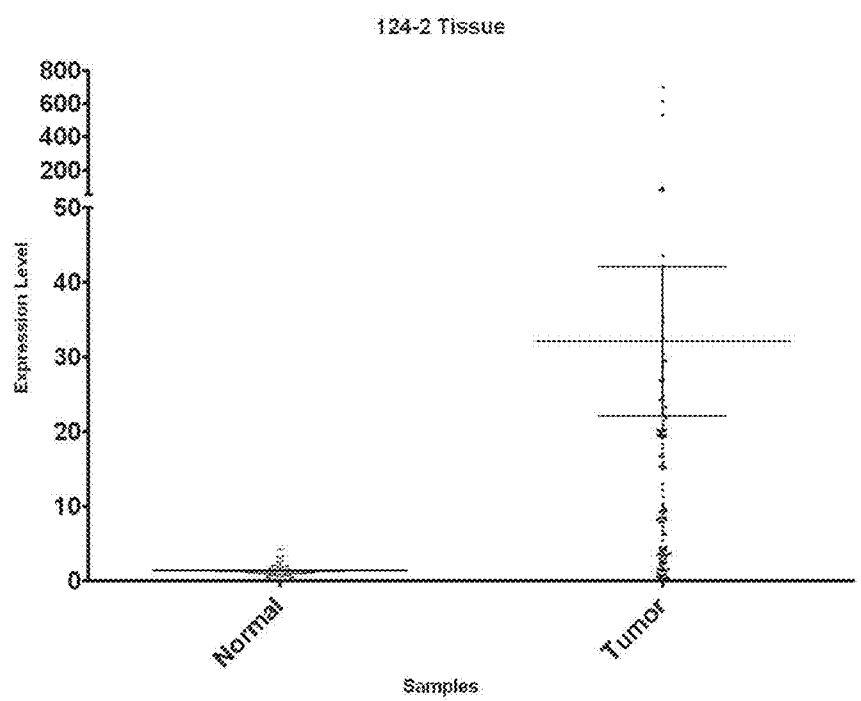
FIG. 4B shows qMS-PCR results that reveal the overall relative methylation level of both the control and subject samples as well as the methylation level of each patient's tumor sample for marker mgmiR124-2.
Figure 5A:
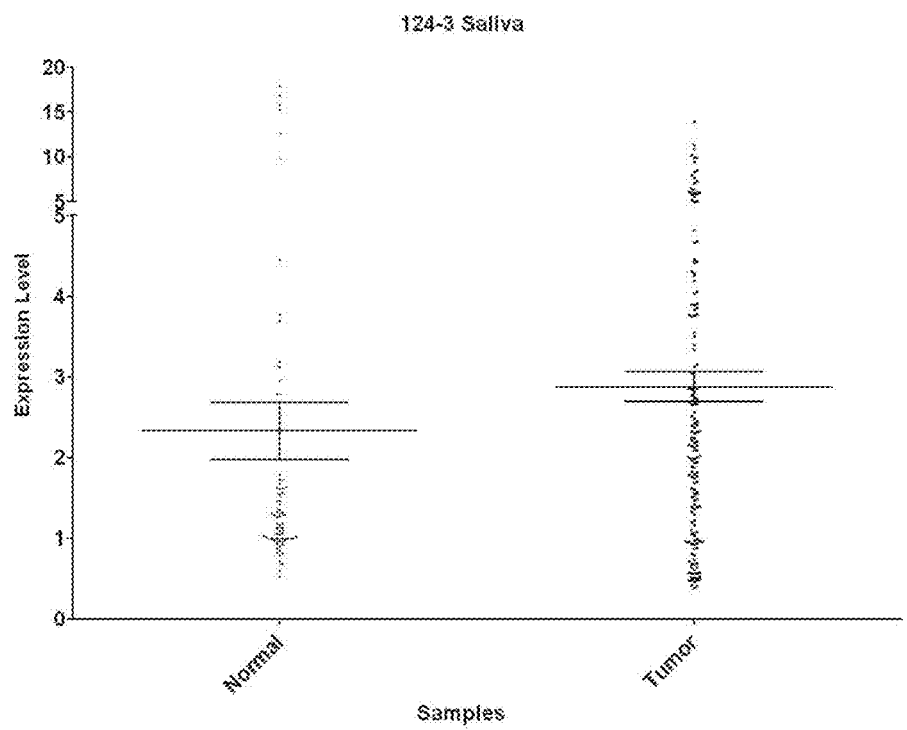
FIG. 5A shows qMS-PCR results that reveal the overall relative methylation level of both the control and subject samples as well as the methylation level of each patient's saliva sample for marker mgmiR124-3.
Figure 5B:
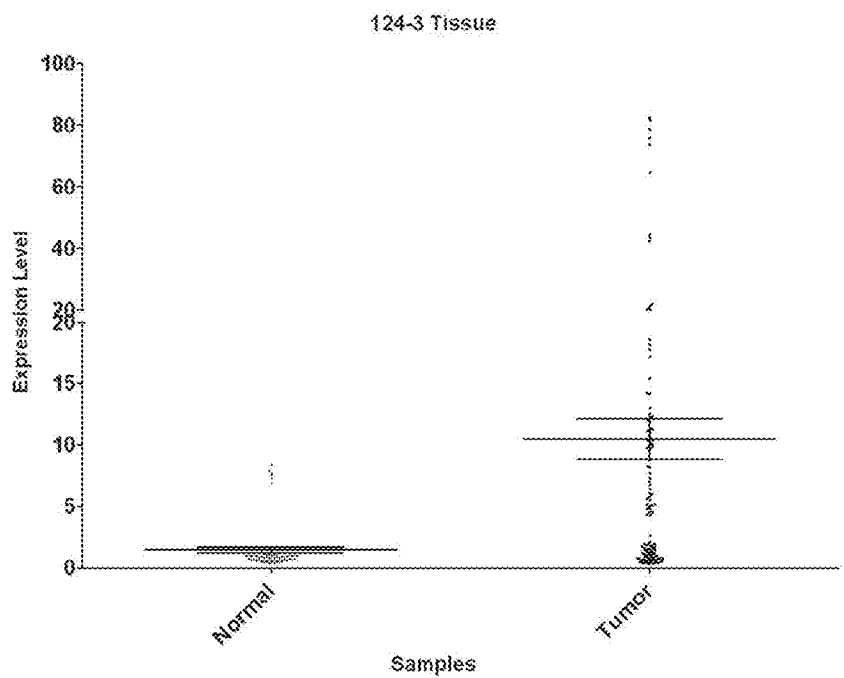
FIG. 5B shows qMS-PCR results that reveal the overall relative methylation level of both the control and subject samples as well as the methylation level of each patient's tumor sample for marker mgmiR124-3.
Figure 6A:
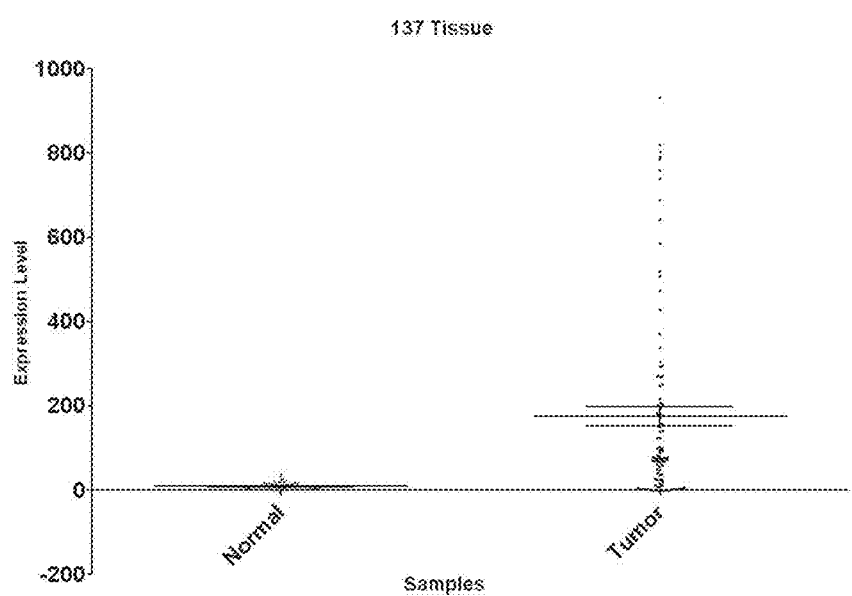
FIG. 6A shows qMS-PCR results that reveal the overall relative methylation level of both the control and subject samples as well as the methylation level of each patient's saliva sample for marker mgmiR137.
Figure 6B:
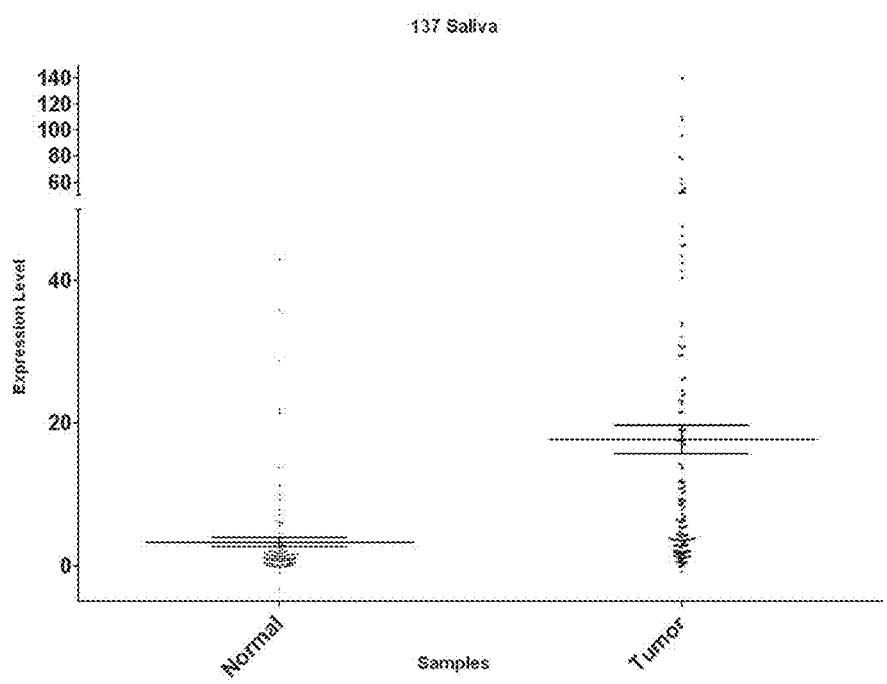
FIG. 6B shows qMS-PCR results that reveal the overall relative methylation level of both the control and subject samples as well as the methylation level of each patient's tumor sample for marker mgmiR137.
Figure 7A:
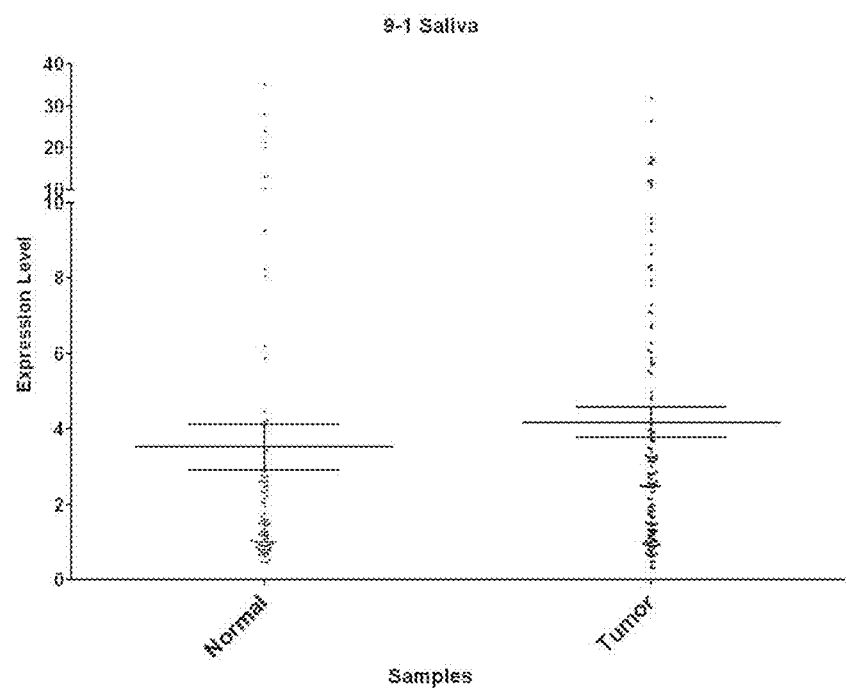
FIG. 7A shows qMS-PCR results that reveal the overall relative methylation level of both the control and subject samples as well as the methylation level of each patient's saliva sample for marker mgmiR9-1.
Figure 7B:
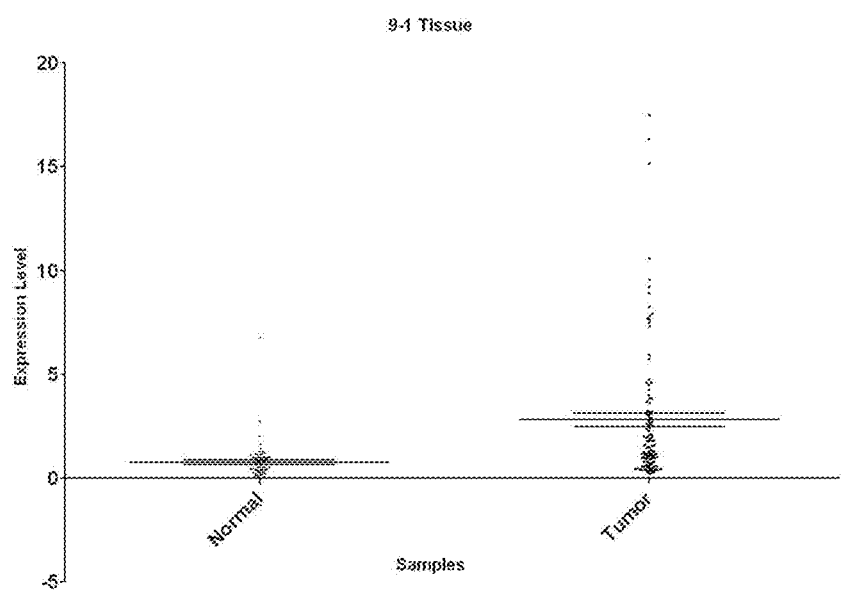
FIG. 7B shows qMS-PCR results that reveal the overall relative methylation level of both the control and subject samples as well as the methylation level of each patient's tumor sample for marker mgmiR9-1.

Disclosed here is a novel method of using qMS-PCR to examine the methylation level of genomic loci encoding microRNAs ("mgmiRs") in HNSCC. After screening more than thirty genomic loci encoding microRNA markers, miR124 (124-1, 124-2 and 124-3), miR137 and miR9 (9-1 and 9-3), proved to be the best markers for detection of HNSCC. This set of 6 markers which, when used as a panel in combination, detected HNSCC with 100% specificity and 90% sensitivity. These markers may act at different sites or via different mechanisms.

In one embodiment, the relative methylation level within the adjacent mucosa group was significantly lower than that of the tumor group. However, compared to the normal control group there was a higher relative methylation level in the adjacent mucosa, and this was statistically significant. This finding has early diagnostic significance as our panel has the potential to detect pre-malignant changes in surrounding tissue. A study by Roh et al in 2011 examined the feasibility of tissue imprinting and the use of qMS-PCR to assess the methylation patterns of 4 genes in the margins of head and neck cancer specimens. Our study examined the presence of microRNA methylation level in adjacent mucosa, and also found that this is a technique with adequate sensitivity and specificity to detect cancer in tissue that appears grossly normal surrounding a tumor.

In another embodiment, as with any test that has an objective numeric outcome, a threshold level may be set above which the test is considered "positive." All of the markers, with the exception of the mgmiR9-1, showed certain level of baseline methylation expression within the cancer-free control group. In order to define and develop our panel for potential clinical use, a threshold methylation level was chosen for each marker. To this end, a weighted Youden Index was used to derive the optimal cutoff for each mgmiR marker.

The term "cancer" refers to a group of diseases involving abnormal cell growth that may invade or spread to other parts of the body. The term "pre-cancer" refers to a state in which a malignant tumor, or hyperplasia/dysplasia may have formed but have not started to or gained the capability to invade or spread to other parts of the body.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1 Development of a Diagnostic Panel of mgmiR Biomarkers for Head and Neck Cancer Material and Methods: This study was conducted on human HNSCC surgical samples in compliance with the Institutional Review Board (IRB) approved protocols from relevant institutions. A total of 64 different tissue specimens were used (n=64). Table 1 shows the breakdown of the study population. Thirty samples were HNSCC specimens from the time of surgical resection (n=30 tumor specimens). This group constituted our "Tumor" group. 26 of these patients also had grossly normal tissue that was collected at the time of surgery from an area adjacent to the primary tumor. These specimens comprised our "adjacent mucosa" group (n=26), and represent grossly normal appearing tissue with hyperplasia/dysplasia under microscope from patients with known head and neck cancer. Oral tissues from 8 healthy patients with no history of malignancy were used as normal control population (n=8). (Table 1).

TABLE 1

Study Population Groups
Tissue Sample Groups

| | |
|---|---|
| Tumor (T) | N = 30 |
| Adjacent Mucosa (AM) | N = 26 |
| Normal Controls (NN) | N = 8 |

All fresh tumor bank tissues were stored in liquid nitrogen until the time of DNA extraction. Genomic DNA was extracted from each tissue sample using the DNeasy Blood & Tissue kit (Qiagen), and was quantitated using the Nanovue spectrophotometer (GE Healthcare). The genomic DNA was then treated with bisulfate using the EZ DNA Methylation-Gold kit (Zymo) and following the manufacture's instruction.

The bisulfate converted DNAs were subjected to the SYBR-green based Quantitative Methylation Specific PCR (qMS-PCR) for the six microRNA markers. For each individual marker, the qMS-PCR protocol was optimized prior to beginning running samples, in order to identify the proper annealing temperature and maximize the results to obtain a typical sigmoid result curve. Melting curves together with gel running were applied to determine the specificity of each marker. Variables adjusted included the temperature, number of cycles, and length of each cycle. Beta-actin was used as an internal control. qMS-PCR was running in triplicates on the CFX Connect™ real time detection system (Biorad). For each sample within each marker, a relative methylation level was calculated using the difference in Ct values by the standard $2^{-\Delta\Delta Ct}$ method.

Statistical Analysis of qMS-PCR results. To allow for all qMS-PCR results to be compared, one control patient was set up as a negative control and the methylation level was arbitrarily defined as one for this patient to calibrate the results for all other patients. For each qMS-PCR experiment, three data points (ΔΔCT value, +SD, −SD) were generated from each sample's triplicate on each qMS-PCR experiment.

Receiver operating characteristic (ROC) curve was used to evaluate the performance of each biomarker. A ROC curve is a graphical plot which illustrates the performance of a binary classifier system (in this project, the biomarker of interest) as its discrimination threshold (the cutpoint to be identified) is varying. The area under curve (AUC) for each ROC curve plotted is reported here. A greater AUC value generally indicates a better-performing biomarker. A perfect diagnostic test would have an AUC value of 1.

Youden's Index was used to derive the cutpoint. The optimal cutpoint should maximize Youden's Index. Unweighted Youden's index is defined J=sensitivity+specificity−1. Weighted Youden's Index is defined J=w*sensitivity+(1−w)*specificity, where w represents a given weight. Naturally, unweighted Youden's puts equal emphasis on sensitivity and specificity. To enhance the specificity, we assigned a higher weight to specificity than sensitivity. The optimal cut-points that maximize the two Youden's were identified, respectively. For the weighted Youden's, a 20% weight to sensitivity and an 80% weight to specificity (in an unweighted Youden sensitivity and specificity can be considered as both having 50% weight) were arbitrarily assigned.

A two-tailed t-test with unequal variance was then used to calculate the significance of differences among the normal control, adjacent mucosa, and tumor groups. Significance was tested for each marker individually, and for the panel as a whole. $p<0.05$ is considered statistically significant.

Results: The relative methylation levels of each methylated microRNA marker as measured by qMS-PCR are shown below and are also summarized in Table 2.

TABLE 2

Percentage of positive methylated microRNA cases in tumor tissues (T), and adjacent mucosa (AM) from HNSCC patients, and normal tissues (NN) from control patients

| | Tumor | Adjacent Mucosa | Normal Mucosa |
|---|---|---|---|
| mgmiR124-1 | 70% (21/30) | 15.4% (4/26) | 0% (0/8) |
| mgmiR124-2 | 70% (21/30) | 3.8% (1/26) | 0% (0/8) |
| mgmiR124-3 | 63.3% (19/30) | 23.1% (6/26) | 0% (0/8) |
| mgmiR137 | 60% (18/30) | 3.8% (1/26) | 0% (0/8) |
| mgmiR9-1 | 56.7% (17/30) | 11.5% (3/26) | 0% (0/8) |
| mgmiR9-3 | 46.7% (14/30) | 3.8% (1/26) | 0% (0/8) |
| combination | 90% (27/30) | 42.3% (11/26) | 0% (0/8) | mgmiR 124-1: The relative methylation level of mgmiR124-1 is 6.60 within the normal control population. Within the tumor group the mean relative methylation level was 128.08 (SE 30.62), and within the adjacent mucosa group the mean relative methylation level was 18.14 (SE 6.13) (FIG. 1A).

mgmiR 124-2: The relative methylation level of mgmiR124-2 is 6.29 within the normal control population. Within the tumor group the mean relative methylation level was 40.21 (SE 6.24), and within the adjacent mucosa group the mean relative methylation level was 5.73 (SE 1.23) (FIG. 1B).

mgmiR124-3: The relative methylation level of mgmiR124-3 is 4.37 within the normal control population. Within the tumor group the mean relative methylation level was 57.66 (SE 16.29), and within the adjacent mucosa group the mean relative methylation level was 18.22 (SE 7.57) (FIG. 1C).

mgmiR 137: The relative methylation level of mgmiR137 is 3.19 within the normal control population. Within the tumor group the mean relative methylation level was 109.30 (SE 25.31), and within the adjacent mucosa group the mean relative methylation level was 8.08 (SE 0.82) (FIG. 1D).

mgmiR 9-1: mgmiR 9-1 was the only marker in the group that showed no baseline methylation level within the control population, and methylation level was found only in cancer specimens. Within the tumor group the mean relative methylation level was 25.14 (Standard Error (SE) 7.44), and within the adjacent mucosa group the mean relative methylation level was 1.80 (SE 0.79) (FIG. 1E).

mgmiR 9-3: The relative methylation level of mgmiR9-3 is 1.76 within the normal control population. Within the tumor group the mean relative methylation level was 9.50 (SE 2.81), and within the adjacent mucosa group the mean relative methylation level was 1.03 (SE 0.27) (FIG. 1F).

Combination of 6 biomarkers: When comparing the relative methylation level of all 6 mgmiR markers as a whole, the relative methylation signal was 3.70 for the normal control population, and 61.65 for the tumor population. This difference was statistically significant ($p<0.001$). The relative methylation level in the adjacent mucosa was 8.63. When compared to the methylation level of the normal controls, this difference also demonstrated statistical significance ($p=0.005$).

After the relative methylation level of the six mgmiR biomarkers had been measured, a receiver operating characteristic curve and a weighted Youden's Index to derive the cut-off value were used. For more details, refer to the Material and Methods section above. These calculations were done from the qPCR results for each marker and each sample.

Using these 6 markers in a combined panel, these results showed 90% sensitivity and 100% specificity in the detection of squamous cell carcinoma within 30 tumor specimens (FIG. 2a). Interestingly, within the adjacent mucosa specimens, the sensitivity was 42.3% and the specificity was 100% for the detection of squamous cell carcinoma (FIG. 2b).

Example 2 Identification and Use of Saliva mgmiRs as Novel Non-Invasive Biomarkers for HNSCC Patients Material and Methods: This study was conducted on human HNSCC tissue samples as well as saliva samples from patients. The study was approved by the Institutional Review Board (IRB) and patient's consent was obtained prior to use of sample. Tissue and/or saliva samples were collected from 36 patients.

Tissue and saliva samples were either labeled as subject (tumor) or control. The subject group consisted of patients that had a diagnosis concerning for HNSCC. Tissue and saliva was obtained from 24 HNSCC patients. Tissue from these patients was confirmed to be HNSCC tissue based on clinical exam and/or previous biopsies. Tumor tissue was obtained in the operating room when patients underwent either surgical resection or biopsy. Saliva was gathered from patients before they underwent surgical resection.

The control group consisted of patients who are cancer-free. Tissue and saliva was obtained from 12 control patients undergoing tonsillectomy. Indications for tonsillectomy were either for obstructive sleep apnea and/or chronic tonsillitis. Tissue was collected in the operating room and consisted of normal mucosa from the anterior tonsillar pillar and/or tonsil tissue. Saliva was gathered from patients before they underwent surgical resection. Saliva was also collected from five disease-free healthy volunteers.

Demographic information of patients in this study was gathered as well as use of tobacco products and alcohol, any previous chemotherapy and/or radiation, history of cancer, and family history of cancer. In the subject group information regarding the clinical stage and grade of the tumor tissue as well as pathologic features and molecular markers was also reviewed and compiled once pathology was finalized for the tissue samples. All information collected was placed in an encrypted database and samples were listed without patient identifiers.

After harvesting, tissue was immediately taken to the laboratory where it was frozen and stored in liquid Nitrogen until later DNA extraction. 30 minutes before saliva collection, patients/volunteers need to stop taking food, drinking, chewing gums and smoking. By the time of saliva collection, patients rinsed their mouths with normal saline for two times with interval of 2 minutes. Patients/volunteers were then instructed to spit their saliva into a Falcon 50 ml collection tubes for 2-3 times with an interval of 2 minutes for 2-3 times. approximately, 4-5 mL of saliva was obtained from the majority of patients with some samples has limited volume due to xerostomia. Once collected, samples were taken to the laboratory, where it was stored in a −20 degree Celsius freezer.

Isolation of genomic DNAs and bisulfite conversion. Genomic DNA was extracted from each tissue sample using the DNeasy Blood & Tissue kit (Qiagen) according to the manufacture's instruction. For saliva genomic DNA extraction, the frozen saliva samples were melted slowly at room temperature, and were added additional 5 ml saliva preparation buffer to each saliva sample for stabilization of genomic DNA at room temperature. The saliva samples were then centrifuged with 5000 rpm for 15 minutes. Five different genomic DNA extraction kits were tested. The QiaAmp DNA mini kit gave the best yield and quality of genomic DNA from saliva. The genomic DNA was then quantitated using the Nanovue spectrophotometer (GE Healthcare). The genomic DNA was then treated with bisulfite using the EZ DNA Methylation-Gold kit (Zymo) and following the manufacture's instruction.

Quantitative Methylation Specific PCR (qMS-PCR). The bisulfate converted DNAs were subjected to the SYBR-green based qMS-PCR for the six microRNA markers (primer sequences for the qMS-PCR are as shown in SEQ ID NOs. 1-12). For each individual marker, the qMS-PCR protocol was optimized prior to beginning running samples, in order to identify the proper annealing temperature and maximize the results to obtain a typical sigmoid result curve. Melting curves together with gel running were applied to determine the specificity of each marker. qMS-PCR was running using SYBR green mix (Biorad) under the following thermo condition: 95C 3 min, 95C 30 sec, 55-60C 30 sec for 40 cycles. Beta-actin was used as an internal control. qMS-PCR was running in triplicates on the CFX Connect™ real time detection system (Biorad). For each sample within each marker, a relative methylation level was calculated using the difference in Ct values by the standard $2^{-\Delta\Delta Ct}$ method.

Statistical Analysis of qMS-PCR results. To allow for all qMS-PCR results to be compared, one control patient was set up as a negative control and the methylation level was arbitrarily defined as one for this patient to calibrate the results for all other patients. For each qMS-PCR experiment, three data points (ΔΔCT value, +SD, −SD) were generated from each sample's quadruplicate on each qMS-PCR experiment.

Receiver operating characteristic (ROC) curve was used to evaluate the performance of each biomarker. A ROC curve is a graphical plot which illustrates the performance of a binary classifier system (in this project, the biomarker of interest) as its discrimination threshold (the cutpoint to be identified) is varying. The area under curve (AUC) for each ROC curve plotted is reported. A greater AUC value generally indicates a better-performing biomarker. A perfect diagnostic test would have an AUC value of 1.

Youden's Index was used to derive the cutpoint. The optimal cutpoint should maximize Youden's Index. Unweighted Youden's index is defined J=sensitivity+specificity−1. Weighted Youden's Index is defined J=w*sensitivity+(1−w)*specificity, where w represents a given weight. Naturally, unweighted Youden's puts equal emphasis on sensitivity and specificity. To enhance the specificity, a higher weight was assigned to specificity than sensitivity. The optimal cut-points that maximize the two Youden's were then identified, respectively. For the weighted Youden's, a 20% weight was arbitrarily assigned to sensitivity and an 80% weight to specificity (in an unweighted Youden sensitivity and specificity can be considered as both having 50% weight).

A two-tailed t-test with unequal variance was then used to calculate the significance of differences among the normal control, adjacent mucosa, and tumor groups. Significance was tested for each marker individually, and for the panel as a whole. $p<0.05$ is considered statistically significant.

Figure 8:
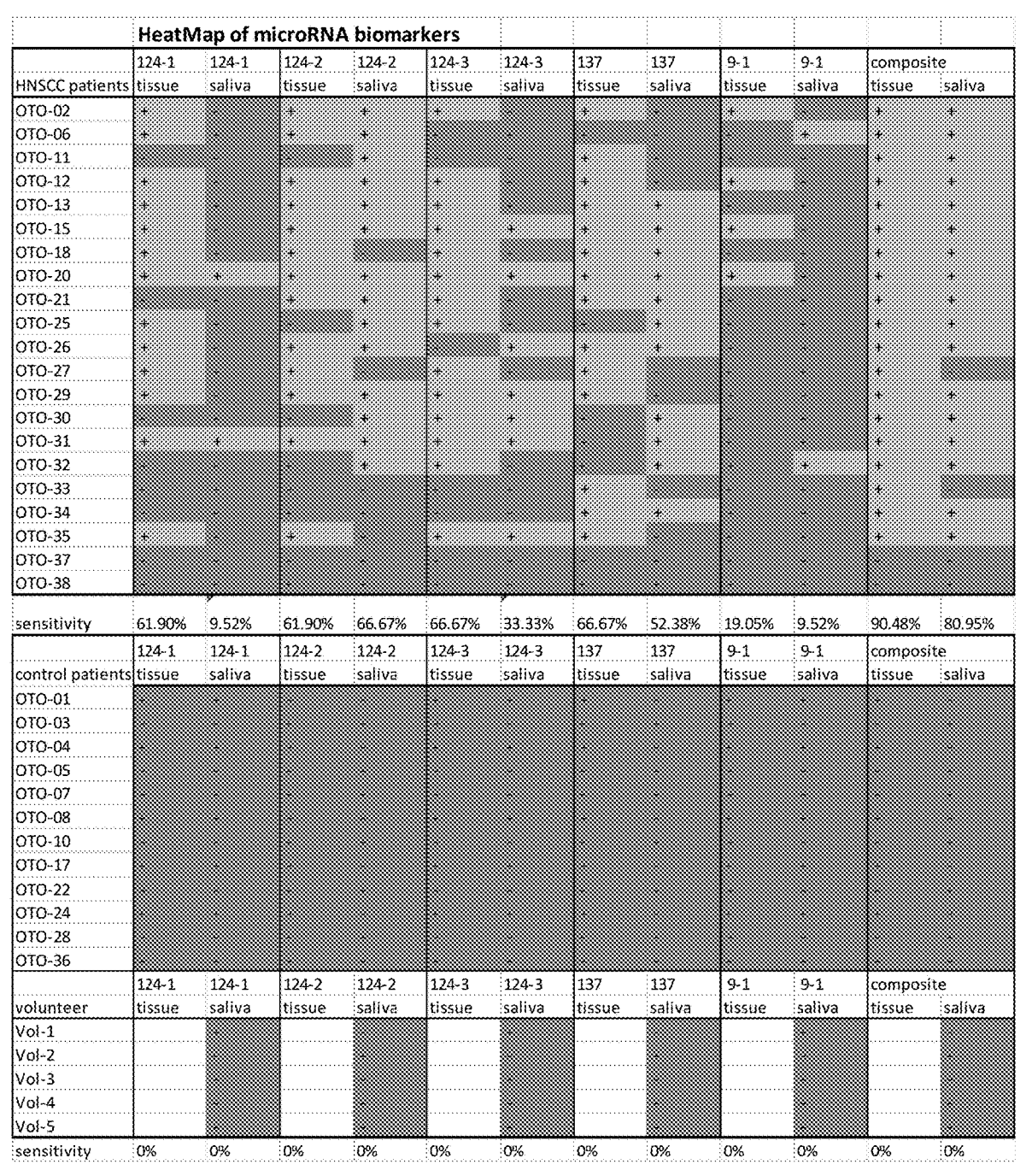

The following five mgmiRs were analyzed: mgmiR124-1, 2, 3, mgmiR137, and mgmiR9-1. Shown in FIGS. 3A, 3B, 4A, 4B, 5A, 5B, 6A 6B, 7A, and 7B are qMS-PCR results that reveal the overall relative methylation level of both the control and subject samples as well as the methylation level of each patient's saliva and tumor sample for each marker. FIG. 8 shows the HeatMap of comparison of these mgmiR biomarkers. Sensitivity and specificity were calculated for each miRNA marker in the saliva and the tissue samples using Youden's index. Also, overall sensitivity and specificity was determined when all miRNA markers were used together. These results are listed in Table 3 and Table 4.

TABLE 3

Sensitivity and specificity in HNSCC patients' tissues

| Tested Biomarker | Area under the Curve | Sensitivity at Maximum Unweighted Youden's Index | Specificity at Maximum Unweighted Youden's Index | Maximum Unweighted Youden's Index | Optimal Cutoff Based on Maximum Unweighted Youden's Index | Sensitivity at Maximum Weighted Youden's Index | Specificity at Maximum Weighted Youden's Index | Maximum Weighted Youden's Index | Optimal Cutoff Based on Maximum Weighted Youden's Index |
|---|---|---|---|---|---|---|---|---|---|
| mgmiR124-1 | 0.8333 | 68.2% | 100% | 0.68182 | −1.50375 | 68.2% | 100% | 0.93636 | −1.50375 |
| mgmiR124-2 | 0.7955 | 63.6% | 100% | 0.63636 | −0.43000 | 63.6% | 100% | 0.92727 | −0.43000 |
| mgmiR124-3 | 0.8258 | 68.2% | 100% | 0.68182 | 0.35250 | 68.2% | 100% | 0.93636 | 0.35250 |
| mgmiR137 | 0.7803 | 68.2% | 100% | 0.68182 | −2.54667 | 68.2% | 100% | 0.93636 | −2.54667 |
| mgmiR9-1 | 0.6925 | 66.7% | 66.7% | 0.33333 | 2.21000 | 19.0% | 100% | 0.83810 | −0.48317 |
| Combine | | | | | | 90.5% | 100% | | |

TABLE 4

Sensitivity and specificity in HNSCC patients' saliva

| Tested Biomarker | Area under the Curve | Sensitivity at Maximum Unweighted Youden's Index | Specificity at Maximum Unweighted Youden's Index | Maximum Unweighted Youden's Index | Optimal Cutoff Based on Maximum Unweighted Youden's Index | Sensitivity at Maximum Weighted Youden's Index | Specificity at Maximum Weighted Youden's Index | Maximum Weighted Youden's Index | Optimal Cutoff Based on Maximum Weighted Youden's Index |
|---|---|---|---|---|---|---|---|---|---|
| mgmiR124-1 | 0.5602 | 41.7% | 77.8% | 0.19444 | −0.80000 | 0.08333 | 100% | 0.81667 | −1.85588 |
| mgmiR124-2 | 0.8102 | 66.7% | 100% | 0.66667 | −0.54500 | 0.66667 | 100% | 0.93333 | −0.54500 |
| mgmiR124-3 | 0.7500 | 79.2% | 64.7% | 0.43873 | 1.58875 | 0.33333 | 100% | 0.86667 | 0.10375 |

TABLE 4-continued

Sensitivity and specificity in HNSCC patients' saliva

| Tested Biomarker | Area under the Curve | Sensitivity at Maximum Unweighted Youden's Index | Specificity at Maximum Unweighted Youden's Index | Maximum Unweighted Youden's Index | Optimal Cutoff Based on Maximum Unweighted Youden's Index | Sensitivity at Maximum Weighted Youden's Index | Specificity at Maximum Weighted Youden's Index | Maximum Weighted Youden's Index | Optimal Cutoff Based on Maximum Weighted Youden's Index |
|---|---|---|---|---|---|---|---|---|---|
| mgmiR137 | 0.7708 | 62.5% | 83.3% | 0.45833 | −0.95750 | 0.45833 | 100% | 0.89167 | −1.62375 |
| mgmiR9-1 | 0.5185 | 45.8% | 77.8% | 0.23611 | −0.10833 | 0.08333 | 100% | 0.81667 | −1.28667 |
| Combine | | | | | | 81% | 100% | | |

Sensitivity and specificity were calculated for the samples based on HPV and EGFR status, anatomical site of the primary as well as pathologic grade and stage of tumor.

One purpose of this study was to investigate whether patients with HNSCC had higher rates of methylation in five genomic loci for specific miRNAs (miR124-1, 124-2, 124-3, 137, 9-1) that may have tumor suppressor roles. It was hypothesized that this difference could be detected not only in tissue samples, but also from the patient's saliva.

The disclosed data revealed a disparity in methylation between the subject and control samples. Comparison of all control and subject tissue samples demonstrated a significant difference in methylation for all five mgmiRNAs. Similarly, when control and tissue saliva samples were compiled and compared, higher levels of methylation for all five mgmiRNAs were observed, with 124-1, 124-2, and 137 showing a significant difference between control and subject samples. The higher level of methylation in the subject population may highlight a downregulation of their corresponding encoded miRNAs and underline their possible suppressor role in tumorigenesis.

Breaking the methylation data further down into each individual control and subject sample, further illustrated this trend that subject samples had higher levels of methylation than the control samples. Sensitivity and specificity values demonstrated that in the saliva samples the mgmiR124-2 was the most sensitive miRNA marker followed by 137, 124-3, 9-1, and 124-1. In tissue samples, mgmiR124-2 was also the most sensitive miRNA marker followed by 137, 124-1, 124-3, and 9-1. The tissue samples were overall more sensitive than the saliva samples with all five miRNA markers having a greater than 50% sensitivity in the tissue samples. The specificity of the mgmiR markers was much higher in both the tissue and saliva samples with all having greater than 80% specificity. Of the ten miRNA markers (5 saliva and 5 tissue), six had a specificity of 100%.

Overall, more tissue samples were positive than saliva samples. This result was not unexpected as the tissue should contain robust HNSCC DNA while the saliva samples may contain certain HNSCC DNA from tumor desquamation. Interestingly, there is strong relationship with over 80% of the saliva samples that were positive also being positive in their correlating tissue samples. The most powerful results from these data were the calculation of the overall sensitivity and specificity when all five miRNAs were used together. This result suggests potential application of these findings in a DNA microarray. When this is done, sensitivity and specificity for saliva samples are 81% and 100% and sensitivity and specificity for tissue samples are 90.5% and 100%, respectively (Table 3-4).

Using clinical and pathological information, the subject samples were analyzed independently based on multiple different variables. FIG. 9 shows the correlation between biomarkers and human papilloma virus (HPV) status. FIG. 10 shows the correlation between biomarkers and EGFR status. FIG. 11 shows the correlation between biomarkers and anatomic sites. FIG. 12 shows the correlation between biomarkers and pathological status.

Overall, sensitivity and specificity was equal or greater in both the saliva and tissue samples in that were HPV+ and/or EGFR+. The subject's samples were also evaluated based on anatomic site of the primary tumor as well as pathologic grade and clinic stage. Comparing samples based on these variables did not delineate a specific trend in regard to sensitivity or specificity given the relatively smaller sample size, which should be significantly improved when sample size is increased for statistical analysis.

In this study, it was revealed that specific tumor suppressor miRNAs with presumed tumor suppressor roles appear to have higher rates of DNA methylation in patients with HNSCC compared to control patients. This discrepancy in methylation can be detected in both patient's tissue and saliva and may underline a role of these miRNAs in tumorigenesis. Furthermore, this epigenetic difference can be potentially used as a diagnostic test with data from this study demonstrating an overall sensitivity and specificity of over 90% in tissue and saliva samples. This finding underlines the potential future ability to use epigenetic alterations of miRNA genomes as a diagnostic screening test for HNSCC.

REFERENCES

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of immunology, molecular biology and cell biology, which are well known in the art.

The present disclosure also incorporates by reference in their entirety techniques and methods well known in the field of molecular biology. These techniques include, but are not limited to, techniques described in the following publications.

1. Watson J D, Crick F H. Molecular structure of nucleic acids; a structure for deoxyribose nucleic acid. Nature. 1953; 171(4356):737-8.
2. Lee R C, Feinbaum R L, Ambros V. The C. elegans heterochronic gene lin-4 encodes small RNAs with antisense complementarity to lin-14. Cell. 1993; 75(5):843-54.
3. Ambros V. The functions of animal microRNAs. Nature. 2004; 431(7006):350-5.

4. Lewis, B., Shih, I., Jones-Rhoades, M., Bartel, D.& Burge, C. Prediction of mammalian microRNA targets. Cell 115, 787-798 (2003).
5. Krek, D. et al. Combinatorial microRNA target predictions. Nature Genet. 37, 495-500 (2005).
6. Betel, D., Wilson, M., Gabow, A., Marks, D. S. & Sander, C. The microRNA.org resource: targets and expression. Nucleic Acids Res. 36, D149-D153 (2008).
7. Friedman, R. C., Farh, K. K., Burge, C. B. & Bartel, D. P. Most mammalian mRNAs are conserved targets of microRNAs. Genome Res. 19, 92-105 (2009).
8. Garzon R, Marcucci G, Croce CM. Targeting microRNAs in cancer: rationale, strategies and challenges. Nat Rev Drug Discov. 2010; 9(10):775-89.
9. Worsham M J, Ali H, Dragovic J, Schweitzer V P. Molecular characterization of head and neck cancer: how close to personalized targeted therapy?. Mol Diagn Ther. 2012; 16(4):209-22.
10. Minor J, Wang X, Zhang F, et al. Methylation of microRNA-9 is a specific and sensitive biomarker for oral and oropharyngeal squamous cell carcinomas. Oral Oncol. 2012; 48(1):73-8.
11. Boyle J O, Mao L, Brennan J A, et al. Gene mutations in saliva as molecular markers for head and neck squamous cell carcinomas. Am J Surg. 1994; 168(5):429-32.
12. Worsham M J, Chen K M, Ghanem T, Stephen J K, Divine G. Epigenetic modulation of signal transduction pathways in HPV-associated HNSCC. Otolaryngol Head Neck Surg. 2013; 149(3):409-16.
13. Jemal, A.; Siegel, R.; Ward, E.; Hao, Y.; Xu, J.; Thun, M. J., Cancer statistics, 2009. *CA: a cancer journal for clinicians* 2009, 59 (4), 225-49.
14. Siegel, R.; Naishadham, D.; Jemal, A., Cancer statistics, 2013. *CA: a cancer journal for clinicians* 2013, 63 (1), 11-30.
15. Jemal, A.; Siegel, R.; Ward, E.; Hao, Y.; Xu, J.; Thun, M. J., Cancer statistics, 2009. *CA: a cancer journal for clinicians* 2009, 59 (4), 225-49.
16. Siegel, R.; Naishadham, D.; Jemal, A., Cancer statistics, 2013. *CA: a cancer journal for clinicians* 2013, 63 (1), 11-30.
17. Iorio, M. V.; Croce, C. M., MicroRNA dysregulation in cancer: diagnostics, monitoring and therapeutics. A comprehensive review. *EMBO Mol Med* 2012, 4 (3), 143-59.
18. Croce, C. M., Causes and consequences of microRNA dysregulation in cancer. *Nat Rev Genet* 2009, 10 (10), 704-14.
19. Lujambio, A.; Calin, G. A.; Villanueva, A.; Ropero, S.; Sanchez-Cespedes, M.; Blanco, D.; Montuenga, L. M.; Rossi, S.; Nicoloso, M. S.; Faller, W. J.; Gallagher, W. M.; Eccles, S. A.; Croce, C. M.; Esteller, M., A microRNA DNA methylation signature for human cancer metastasis. *Proc Natl Acad Sci U S A* 2008, 105 (36), 13556-61.
20. (a) Gangaraju, V. K.; Lin, H., MicroRNAs: key regulators of stem cells. *Nat Rev Mol Cell Biol* 2009, 10 (2), 116-25; (b) Rosenfeld, N.; Aharonov, R.; Meiri, E.; Rosenwald, S.; Spector, Y.; Zepeniuk, M.; Benjamin, H.; Shabes, N.; Tabak, S.; Levy, A.; Lebanony, D.; Goren, Y.; Silberschein, E.; Targan, N.; Ben-Ari, A.; Gilad, S.; Sion-Vardy, N.; Tobar, A.; Feinmesser, M.; Kharenko, O.; Nativ, O.; Nass, D.; Perelman, M.; Yosepovich, A.; Shalmon, B.; Polak-Charcon, S.; Fridman, E.; Avniel, A.; Bentwich, I.; Bentwich, Z.; Cohen, D.; Chajut, A.; Barshack, I., MicroRNAs accurately identify cancer tissue origin. *Nat Biotechnol* 2008, 26 (4), 462-9.
21. Iorio, M. V.; Piovan, C.; Croce, C. M., Interplay between microRNAs and the epigenetic machinery: an intricate network. *Biochim Biophys Acta* 2010, 1799 (10-12), 694-701.
22. Saito, Y.; Liang, G.; Egger, G.; Friedman, J. M.; Chuang, J. C.; Coetzee, G. A.; Jones, P. A., Specific activation of microRNA-127 with downregulation of the proto-oncogene BCL6 by chromatin-modifying drugs in human cancer cells. *Cancer Cell* 2006, 9 (6), 435-43.
23. Hildebrandt, M. A.; Gu, J.; Lin, J.; Ye, Y.; Tan, W.; Tamboli, P.; Wood, C. G.; Wu, X., Hsa-miR-9 methylation status is associated with cancer development and metastatic recurrence in patients with clear cell renal cell carcinoma. *Oncogene* 29 (42), 5724-8.
24. Saito, Y.; Jones, P. A., Epigenetic activation of tumor suppressor microRNAs in human cancer cells. *Cell Cycle* 2006, 5 (19), 2220-2.
25. Minor, J.; Wang, X.; Zhang, F.; Song, J.; Jimeno, A.; Wang, X. J.; Lu, X.; Gross, N.; Kulesz-Martin, M.; Wang, D.; Lu, S. L., Methylation of microRNA-9 is a specific and sensitive biomarker for oral and oropharyngeal squamous cell carcinomas. *Oral Oncol* 2012, 48 (1), 73-8.
26. Jones, P. A.; Baylin, S. B., The epigenomics of cancer. *Cell* 2007, 128 (4), 683-92.
13. Ha, P. K.; Califano, J. A., Promoter methylation and inactivation of tumour-suppressor genes in oral squamous-cell carcinoma. *Lancet Oncol* 2006, 7 (1), 77-82.
27. Babu, J. M.; Prathibha, R.; Jijith, V. S.; Hariharan, R.; Pillai, M. R., A miR-centric view of head and neck cancers. *Biochim Biophys Acta* 2011, 1816 (1), 67-72.
28. Roh, J. L.; Westra, W. H.; Califano, J. A.; Sidransky, D.; Koch, W. M., Tissue imprint for molecular mapping of deep surgical margins in patients with head and neck squamous cell carcinoma. *Head Neck* 2012, 34 (11), 1529-36.

The invention claimed is:

1. A method for detecting head and neck cancer in a human subject, comprising
    (a) preparing genomic DNA extract comprising a genomic locus encoding a microRNA (mgmiR) from a tissue or body fluid of said human subject, said genomic DNA extract comprising a first DNA fragment encompassing a genomic locus encoding a microRNA 137, said tissue or body fluid being selected from the group consisting of a head tissue, a neck tissue, mouth swab, nose swab, saliva, and combination thereof,
    (b) generating a second DNA fragment by quantitative polymerase chain reaction (qPCR) using as a template said first DNA fragment and using as primers oligonucleotide pair having the sequence SEQ ID Nos. 7 and 8 for microRNA 137,
    (c) measuring the level of said second DNA fragment generated in step (b), and
    (d) comparing the level of said second DNA fragment with a base level, said base level being the level of a corresponding DNA fragment generated by the same manner from the same tissue or body fluid of an individual known to be free from said cancer, wherein at least 60% higher level of said second DNA fragment as compared to said base level is indicative of head and neck cancer in said human subject.

2. The method of claim 1, wherein said head and neck cancer is a head and neck squamous cell carcinoma (HNSCC).

3. The method of claim 1, further comprising a step (e) of treating said human subject with a treatment method selected from the group consisting of surgery, chemotherapy, radiation therapy, and combination thereof.

4. The method of claim 1, wherein a 100% higher level of said second DNA fragment as compared to the base level is indicative of presence of cancer.

\* \* \* \* \*